US009241876B2

(12) United States Patent
Zheng et al.

(10) Patent No.: US 9,241,876 B2
(45) Date of Patent: Jan. 26, 2016

(54) ARIPIPRAZOLE MEDICAMENT FORMULATION AND PREPARATION METHOD THEREFOR

(75) Inventors: Siji Zheng, Shanghai (CN); Xiaoyi Liu, Shanghai (CN); Linyong Fu, Shanghai (CN); Bo Tan, Shanghai (CN); Min Zhou, Shanghai (CN)

(73) Assignee: SHANGHAI ZHONGXI PHARMACEUTICAL CORPORATION, Shanghai (CN)

( * ) Notice: Subject to any disclaimer, the term of this patent is extended or adjusted under 35 U.S.C. 154(b) by 0 days.

(21) Appl. No.: 14/129,713

(22) PCT Filed: Jun. 26, 2012

(86) PCT No.: PCT/CN2012/077511
§ 371 (c)(1),
(2), (4) Date: Dec. 27, 2013

(87) PCT Pub. No.: WO2013/000391
PCT Pub. Date: Jan. 3, 2013

(65) Prior Publication Data
US 2014/0135343 A1    May 15, 2014

(30) Foreign Application Priority Data

Jun. 27, 2011   (CN) .......................... 2011 1 0180018

(51) Int. Cl.
| | | |
|---|---|---|
| A61K 31/496 | (2006.01) |
| A61J 3/02 | (2006.01) |
| A61K 47/02 | (2006.01) |
| A61K 9/00 | (2006.01) |
| A61K 9/10 | (2006.01) |
| A61K 9/16 | (2006.01) |
| A61K 9/20 | (2006.01) |
| A61K 31/517 | (2006.01) |

(52) U.S. Cl.
CPC ................. *A61J 3/02* (2013.01); *A61K 9/0095* (2013.01); *A61K 9/10* (2013.01); *A61K 9/1611* (2013.01); *A61K 9/1635* (2013.01); *A61K 9/2009* (2013.01); *A61K 9/2027* (2013.01); *A61K 31/496* (2013.01); *A61K 31/517* (2013.01); *A61K 47/02* (2013.01)

(58) Field of Classification Search
CPC .................................................. A61K 31/496
See application file for complete search history.

(56) References Cited

U.S. PATENT DOCUMENTS

| | | | |
|---|---|---|---|
| 6,977,257 B2 | 12/2005 | Parab et al. |
| 2005/0152981 A1 | 7/2005 | Gleeson et al. |
| 2006/0057073 A1 * | 3/2006 | Lintz et al. ..................... 424/45 |
| 2011/0166352 A1 | 7/2011 | Gleeson et al. |
| 2013/0161848 A1 | 6/2013 | Gleeson et al. |

FOREIGN PATENT DOCUMENTS

| | | |
|---|---|---|
| CN | 1871007 A | 11/2006 |
| CN | 101172966 A | 5/2008 |
| CN | 102106806 A | 6/2011 |
| CN | 102106807 A | 6/2011 |
| CN | 102106826 A * | 6/2011 |
| CN | 102846543 A | 1/2013 |
| GB | 2505859 A | 3/2014 |
| WO | WO 2005/041970 A1 | 5/2005 |

OTHER PUBLICATIONS

Ika. "Colloid Mill MK." (c) Sep. 2011. Available from: < http://web.archive.org/web/20110921160445/http://www.ikaprocess.com/Products/Inline-disperser-dispersing-machine-high-shear-cph-6/Colloid-Mill-MK-csb-MK/ >.*
Ika. "HPH." (c) Nov. 29, 2011. Available from: < http://web.archive.org/web/20111129014400/http://www.ikaprocess.com/Products/High-press-homogenizer-cph-43/HPH-csb-HPH >.*
Reddy, G.V., et al. "Identification of degradation products in Aripiprazole tablets by LC-QToF mass spectrometry." European J. of Chemistry. 1 (1), (2010), pp. 20-27.*
Office Action issued in Chinese Patent Application 201210235157.3 dated May 28, 2014 (with translation).
Israeli International Stage Application of PCT/CN2012/077511 filed Dec. 26, 2013 submitted under Zheng, Siji.
International Search Report issued in International Patent Application No. PCT/CN2012/07751 dated Sep. 27, 2012 (with translation).
Written Opinion in International Patent Application No. PCT/CN2012/07751 dated Sep. 27, 2012 (with translation).
Office Action issued in Chinese Patent Application No. 201210235157.3 dated Oct. 28, 2013 (with translation).

* cited by examiner

*Primary Examiner* — Andrew D Kosar
*Assistant Examiner* — John S Kenyon
(74) *Attorney, Agent, or Firm* — Oliff PLC

(57) ABSTRACT

The preparation method includes the following steps: dissolving aripiprazole in an acidic solution having an acidifier so as to obtain a medicament having acidic solution; then, performing a wet granulation on or preparing a suspension with the obtained medicament having acidic solution, an alkalizer, and an excipient so as to obtain the aripiprazole medicament formulation; the excipient comprising an antioxidant. The aripiprazole medicament formulation obtained through the preparation method has a significantly reduced amount of related substances, great solubility, great stability, high bioavailability, reduced individual differences, and enhanced wettability and content uniformity of insoluble medicaments.

31 Claims, No Drawings

ARIPIPRAZOLE MEDICAMENT FORMULATION AND PREPARATION METHOD THEREFOR

FIELD OF INVENTION

The present invention relates to aripiprazole medicament formulation and preparation method therefor.

PRIOR ARTS

Aripiprazole whose chemical name is 7-[4-[4-(2,3-dichlorophenyl)-1-piperazinyl]butoxy]-3,4-dihydro-2(1H)-quinolinone, belongs to quinolinone derivatives, and was approved by the FDA in November, 2002 for the treatment of schizophrenia.

Aripiprazole is a water-indissolvable medicament, and only a certain level of fineness of it can ensure quick dissolution, absorptivity and bioavailability of the prepared preparation. For example, the average particle size can just reach about 100 micron when an universal pulverizer is used to pulverize the aripiprazole mechanically and the dissolution characteristic of the prepared preparation is still not ideal. Besides, the process of mechanical pulverization also has the problems of dust, environmental pollution, and great loss etc. And due to the high activity of aripiprazole, it is easy to cause adverse reactions for the operators if inhaling or touching the aripiprazole powder.

For now, processes for reducing the particle size of the aripiprazole through non-mechanical treatment has been reported in some references. Such as that a chinese patent application (publication number: CN1871007) has disclosed a method for preparing the sterile grain of aripiprazole with an average particle size less than 100 micron by the impact jet crystallization which is used to prepare a sterile freezed dried aripiprazole formulation, and also an injectable aripiprazole aqueous suspension formulation. The chinese patent application (publication number: CN101172966A) has disclosed a method for preparing microcrystal of type I crystal of aripiprazole, which includes heating the crude product of aripiprazole and ethanol of about 10 times the amount of aripiprazole to reflux for dissolution, adding low-temperature water and cooling rapidly when stirring, filtrating, washing and drying the precipitated crystals, and then mixing the gained microcrystal of aripiprazole with excipients to obtain formulation. But the above-mentioned operation is relatively complicated, has a great loss and high cost, and when preparing the formulation by mixing the microcrystal with excipients, there still exists issues of dust and high labor protection requirements.

In addition, to a formulation, it also needs to consider whether some performance indicators are excellent or not, such as stability, solubility and the amount of the related substances contained in formulation etc.

Therefore, for an aripiprazole medicament formulation, it is urgent to seek a preparation method of the aripiprazole formulation which can not only overcome the defects of the existing method mentioned above, but ensure various excellent performances as well.

CONTENT OF THE PRESENT INVENTION

The technical problem to be solved in the present invention is that for overcoming the defects which includes dust, serious security risks, complicated operation, high cost, pollution and great loss of the existing preparing method of the aripiprazole medicament formulation, a preparation method of the aripiprazole medicament formulation and the formulation gained by this method have been provided. The method has no security risks, simple operation, less pollution and loss, low cost, good process control, and can obtain the formulation with excellent solubility, stability and less amount of related substances.

To solve the technical problems above, the inventor specially adopts the technology called "Acid-Base Solventing-out Dispersion" (A-BsoD) which includes dissolving the aripiprazole with acidic solution, and then performing the wet granulation with the medicament having acidic solution, alkalizer and excipients which contain antioxidant, restoring aripiprazole to a solid state in the process of granulation, combining the process of dispersing the microcrystal of insoluble medicaments and excipients with wet granulation or preparation of suspension. The method can not only overcome the defects mentioned above in the prior art, but it is worth mentioning that the aripiprazole formulation prepared by this method also has excellent solubility, stability, especially less amount of related substances. The inventor of the present application also discovered that the method has excellent controllability unexpectedly, which means that the aripiprazole formulation with required particle size can be made artificially controlled by utilizing the regular change between the particle size of aripiprazole contained in the obtained product and the preparing conditions and this is more beneficial to ensuring and controlling the solubility of aripiprazole formulation.

Specifically, the invention achieved the above technical effects by the following technical solutions:

The present invention relates to a method for preparing an aripiprazole medicament formulation, which comprises the following steps: dissolving aripiprazole in an acidic solution having an acidifier so as to obtain a medicament having acidic solution; then, performing a wet granulation on or preparing a suspension with the obtained medicament having acidic solution, an alkalizer, and an excipient so as to obtain the aripiprazole medicament formulation; the said excipient comprising an antioxidant.

In the present invention, the said aripiprazole is an active pharmaceutical which is water-indissolvable and weakly alkaline, and the dosage of which can be determined according to the conventional amount of aripiprazole contained in a formulation. If the solid preparation was prepared by wet granulation, the mass of aripiprazole usually counts 1%~20% the mass of the dry materials of wet granulation, preferably 2%~15%. If the formulation is a suspension, the mass of aripiprazole is usually 0.01%~1% the mass of the suspension, preferably 0.05%~0.2%. According to the need, in addition to the aripiprazole, other active pharmaceutical ingredients can also be added for preparing the compound preparations of aripiprazole. The said other active pharmaceutical ingredients can be used in combination and have no adverse effects with the aripiprazole.

In the present invention, the said acidifier refers to the acid reagent that can make the aripiprazole completely dissolved in the acidic solution having an acidifier. According to the common knowledge in the art, the said acidifier should be pharmaceutically acceptable and compatible with the aripiprazole. In the present invention, the said compatibility means coexistence without adverse effects. The said acidifier can be a single acidifier as well as a compound acidifier consisting of more than two components, which can be selected from a variety of acids, such as one or more among inorganic strong acid, inorganic mediate strong acid and organic weak acid, preferably selected from one or more among hydrochloric acid, citric acid, malic acid, lactic acid, hydrobromic acid, nitric acid, sulfuric acid, fumaric acid, succinic acid, maleic acid, acetic acid and phosphoric acid, and more preferably hydrochloric acid, citric acid, lactic acid and malic acid, and the most preferably from hydrochloric acid, or hydrochloric acid and citric acid. The dosage of the said acidifier is at least the minimum dosage which can completely dissolve the aripiprazole, preferably 1~1.2 times the minimum dosage, more preferably 1~1.05 times the minimum dosage. The said minimum dosage refers to the minimal dose of a certain acidifier which can just make the aripiprazole dissolved under the preparation conditions of the same solvent and medicament having acidic solution, and the said minimum dosage can be obtained by simple conventional method: under the preparation conditions of the same solvent and medicament having acidic solution, the minimum dosage is determined by increasing the acidifier's dosage gradually until when the aripiprazole is just dissolved. It has been concluded by many experiments that when the acidifier is hydrochloric acid, the molar ratio of the hydrochloric acid to the aripiprazole is generally 0.9~1.2, preferably 0.95~1.1, more preferably 0.98~1.05. When the acidifier is hydrochloric acid and citric acid, the molar ratio of the hydrochloric acid and citric acid to the aripiprazole is generally 0.9~1.2, preferably 0.95~1.1, and more preferably 0.98~1.05.

In the present invention, the solvent of the said acidic solution having an acidifier may be organic solvent, or a mixture of water and organic solvent, preferably the mixture of water and organic solvent. The said organic solvent is selected from the acceptable solvents in the pharmaceutical field according to the principle that the solubility of the aripiprazole in this organic solvent is better than that in water, and the water-miscible organic solvent is preferred, such as conventionally used water-soluble alcohols in the pharmaceutical field, like ethanol, propylene glycol, glycerin, isopropyl alcohol and tertiary butyl alcohol etc., preferably one or more among ethanol, propylene glycol and glycerol, and ethanol in particular. The dosage of the organic solvent can be selected optionally in the mixture of water and organic solvent. When using aqueous ethanol solution, the concentration of ethanol is preferably 40 wt % or more, more preferably 60 wt % or more. In the present invention, there is no particular requirement to the solvent dosage of the said acidic solution having an acidifier. In generally, the solvent dosage of the acidic solution having an acidifier is at least able to make the aripiprazole completely dissolved and the subsequent of wet granulation or a suspension can be performed, which is usually 2 times the mass of aripiprazole or more, preferably 3~4 times.

Before an alkalizer is added, some other excipients can be added as well, such as one or more among surfactants, solubilizers, the water-soluble carriers and disintegrants etc., then subsequent steps are carried out with the gained medicament having acidic solution or the mixture of the medicament having acidic solution and the above-mentioned excipients, that is wet granulation or preparing a suspension with the alkalizer and excipients. These excipients can be added during or after the preparation of the medicament having acidic solution, and the order of addition is related to miscibility of these excipients and the medicament having acidic solution. The excipients that can be miscible with the medicament having acidic solution and allow the medicament having acidic solution maintaining in solution state rather than forming a turbid liquid or a viscous liquid could be added during or after the preparation of the medicament having acidic solution, while the excipients which can not be miscible with the medicament having acidic solution and can make the medicament having acidic solution transform into a turbid liquid or a viscous liquid from the solution state are usually required to be added after the medicament having acidic solution is prepared. Generally, the said surfactants and/or the solubilizers can be added during or after the preparation of the medicament having acidic solution; the said water-soluble carriers and/or disintegrants are required to be added after the preparation of the medicament having acidic solution, except for the water-soluble carriers which can dissolve in the medicament having acidic solution (such as polyethylene glycol and hydroxypropyl-β-cyclodextrin). If the said water-soluble carriers are added during the preparation of the medicament having acidic solution, the dosage of water-soluble carriers should be lower than the dosage which can ensure the aripiprazole completely dissolve in the acidifier-containing acid solution and then, the water-soluble carriers and/or disintegrants can still be added after the addition of said dosage of water-soluble carriers, and when a large addition is involved, the gained mixture of medicament having acidic solution and excipients would be in the form of a turbid liquid or a viscous liquid. The said surfactants and/or solubilizers in the present invention prefer one or more among povidone, sodium dodecyl sulfate, poloxamer, polyoxyethylenated castor oil, Tween 80 and polyoxyl (40) stearate, more preferably one or more among povidone, sodium dodecyl sulfate, poloxamer and Tween 80. The said water-soluble carriers in the present invention prefer one or more among lactose, mannitol, sucrose, polyethylene glycol (preferably polyethylene glycol 400-8000), hydroxypropyl-β-cyclodextrin, β-cyclodextrin and maltitol, more preferably one or more among lactose, mannitol, polyethylene glycol 6000, hydroxypropyl-β-cyclodextrin and sucrose. The said disintegrants in the present invention prefer one or more among sodium carboxymethyl starch, hydroxypropyl cellulose, cross-linked polyvinylpyrrolidone and crosslinked carboxymethylcellulose sodium, more preferably one or more among sodium carboxymethyl starch, hydroxypropyl cellulose and cross-linked polyvinylpyrrolidone. The dosage of said surfactants and/or solubilizers is preferably 0.01~2 times the mass of aripiprazole, more preferably 0.02~1 times. The dosage of said water-soluble carriers is preferably 1~10 times the mass of aripiprazole. It can increase solubility of aripiprazole in the acidic solution and reduce the solvent dosage when surfactants and/or solubilizers are added according to the above-mentioned procedure, which is beneficial to the subsequent granulation steps. It is especially worth mentioning that it can make the solubility of aripiprazole medicament formulation better when one or more among surfactants, solubilizers and water-soluble carriers, especially water-soluble carriers, is (are) added according to the procedure mentioned above.

Preferably, during the preparation of the medicament having acidic solution, it is beneficial to the dissolution of aripiprazole when the temperature is appropriately increased through heating (such as using a hot water-bath). Generally, the temperature can be increased to 30~85° C. When aqueous ethanol solution is used, the temperature is preferably increased to 30~70° C., more preferably to 40~65° C.

In the present invention, the said alkalizer refers to the reagent which can reduce the acidity of the mixture of the alkalizer and the medicament having acidic solution relative to the acidity of the medicament having acidic solution, such as inorganic strong alkali (such as sodium hydroxide or potassium hydroxide), the salt of weak acid and strong alkali (such as sodium carbonate, potassium carbonate and disodium hydrogen phosphate). The said alkalizer can be a single alkalizer as well as a compound alkalizer consisting of more than two components, and the said alkalizer is most preferably sodium hydroxide and/or sodium carbonate. According to the conventional knowledge in this field, the said alkalizer should be pharmaceutically acceptable and compatible with the aripiprazole. The dosage of the said alkalizer is at least the one that can reduce the acidity of the mixture of the alkalizer and the medicament having acidic solution relative to that of the medicament having acidic solution. To prevent the pH value of the system from increasing drastically when the alkalizer is added, the alkalizer, especially inorganic strong alkali such as sodium hydroxide, is preferably added in the form of alkalizer-containing solution. The alkalizer, such as sodium carbonate, is added in the form of alkalizer-containing solution or dispersed uniformly among the other excipients. The concentration of the alkalizer in the alkalizer-containing solution is preferably 5~20 wt %. The solvent contained in the alkalizer-containing solution can be water or a mixture of water and organic solvent. The said organic solvent is the same as the organic solvent contained in the medicament having acidic solution.

When the subsequent steps require wet granulation, the total dosage of the solvent contained in the medicament having acidic solution and the solution of said alkalizer should be at least the minimum dosage of the granulating liquid required by wet granulation. Generally, the total dosage of the solvent is 5~100% the mass of dry materials of wet granulation, and preferably 10~75%.

A preferred embodiment of the present invention employs any one of the following groups of acidifier and alkalizer.

Type 1: the said acidifier is inorganic strong acid, and the said alkalizer is inorganic strong alkali, such as hydrochloric acid and sodium hydroxide. The molar ratio of the sodium hydroxide to the hydrochloric acid is preferably 0.95~1.05, more preferably 0.99~1.01. At present, in order to control the pH value of the system better after the alkalizer is added and improve the stability of the formulation, after the preparation of the medicament having acidic solution, before or during the time when the alkalizer is added, a reagent acted as a pH buffer should be added after the alkalizer is added, and the said reagent should be pharmaceutically acceptable. The said reagent can be organic weak acid, such as one or more among citric acid, glycine, tartaric acid, malic acid and acetic acid, also can be all kinds of acid salt such as one or more among sodium bisulfite, sodium sulfite, sodium dihydrogen phosphate, disodium hydrogen phosphate and a conjugate base of organic weak acid such as sodium citrate. The dosage of said reagent is preferably 0.1%~0.4% the mass of aripiprazole, more preferably 0.5%~2%.

Type 2: the said acidifier is inorganic strong acid, and the said alkalizer is the salt of weak acid and strong alkali, such as hydrochloric acid and sodium carbonate, or hydrochloric acid and disodium hydrogen phosphate, preferably hydrochloric acid and sodium carbonate. The molar ratio of the sodium carbonate to the hydrochloric acid or the molar ratio of the disodium hydrogen phosphate to the hydrochloric acid is preferably 0.75~1.05, more preferably 0.90~1.01.

Type 3: the said acidifier is organic weak acid, and the said alkalizer is inorganic strong alkali, such as lactic acid and sodium hydroxide. The molar ratio of the sodium hydroxide to the lactic acid is preferably 0.95~1.05, more preferably 0.99~1.01.

Type 4: the said acidifier is inorganic strong acid and organic weak acid, and the said alkalizer is inorganic strong alkali and/or the salt of weak acid and strong alkali. When the acidifier is hydrochloric acid and citric acid, the said alkalizer is preferably sodium hydroxide, or the combination of sodium hydroxide and sodium carbonate. When the acidifier is hydrochloric acid and citric acid and the said alkalizer is sodium hydroxide, the molar ratio of the sodium hydroxide to the acidifier is preferably 0.95~1.05, more preferably 0.99~1.01. When the acidifier is hydrochloric acid and citric acid and the said alkalizer is sodium hydroxide and sodium carbonate, the molar ratio of the alkalizer to the acidifier is preferably 0.95~1.05, more preferably 0.99~1.01.

In the present invention, the said antioxidant can be selected according to the common knowledge in the present field, which can be but not limited to one or more among sodium metabisulfite, sodium bisulfite, sodium sulfite, thiourea, sodium thiosulfate, L-cysteine and sodium ascorbate, water-soluble organic weak acid, the conjugate base of the water-soluble organic weak acid, butylated hydroxyanisole, dibutyl hydroxy toluene, ascorbyl palmitate and propyl gallate etc. The said water-soluble organic weak acid is preferably one or more among citric acid, tartaric acid and malic acid. The said conjugate base of the water-soluble organic weak acid is preferably sodium citrate and/or sodium tartrate.

Wherein the said antioxidant preferably includes antioxidant which can play a role in buffering in the case that the acidifier or alkalizer is excessed, such as one or more among sodium bisulfite, sodium metabisulfite and sodium sulfite etc. which may play a role in pH buffering in the case that the acidifier or alkalizer is excessed, and the water-soluble organic weak acid, such as citric acid etc., can play a role in pH buffering in the case that the alkalizer is excessed.

In the present invention, the antioxidant is preferably the sodium bisulfite, sodium metabisulfite, sodium sulfite or sodium thiosulfate in combination with the said water-soluble organic weak acid, or in combination with the said water-soluble organic weak acid and the conjugated base of this water-soluble organic weak acid. The said combination is preferably sodium sulfite in combination with the said water-soluble organic weak acid, or sodium bisulfite, the said water-soluble organic weak acid in combination with the conjugate base of this water-soluble organic weak acid, more preferably the combination of sodium sulfite and citric acid, or the combination of sodium bisulfite, citric acid and sodium citrate.

The said antioxidant is preferably added after the preparation of the said medicament having acidic solution, and before or during the time when the said alkalizer is added. The dosage of the said antioxidant is preferably 0.1~100% the mass of aripiprazole. When the solid formulation is prepared by wet granulation, the dosage of the said antioxidant is preferably 0.1~10% the mass of aripiprazole, more preferably 1~5% the mass of aripiprazole. When a suspension is prepared, the dosage of the said antioxidant is preferably 10~100% the mass of aripiprazole.

In the present invention, the said wet granulation can be carried on according to the conventional granulation steps and conditions belonging to the category of wet granulation in the field, such as extrusion granulation (e.g. extrusion by swing machine, screw extrusion and rotating extrusion etc.), stirring granulation, fluidized spray granulation, centrifugal spray granulation and so on. Stirring granulation and extrusion granulation are preferred. Preferably, the specific mode of operation is selected from anyone of the following methods: method (1) uniformly mixing the medicament having acidic solution with the alkalizer or the alkalizer-containing solution to obtain a granulating solution, and then carrying on extrusion granulation, stirring granulation, fluidized spray granulation or centrifugal spray granulation with the granulating solution and the excipients to obtain the solid preparations; method (2) uniformly mixing the medicament having acidic solution with the excipients, and then uniformly mixing them with the alkalizer or the alkalizer-containing solution, and carrying on extrusion granulation or stirring granulation to obtain the solid preparations; method (3) uniformly mixing the alkalizer or the alkalizer-containing solution with the excipients, and then uniformly mixing them with the medicament having acidic solution, and carrying on extrusion granulation or stirring granulation to obtain the solid preparations; method (4) uniformly mixing the medicament having acidic solution, the excipients whose dosage are below one-third with the alkalizer or the alkalizer-containing solution, and then mixing them with the left excipients and carrying on extrusion granulation or stirring granulation to obtain the solid preparations. In the methods mentioned above, the said solid preparations can be solid particles preparations, also can be tablets (including the oral disintegrating tablets of aripiprazole), dry suspensions or capsules etc. and other forms of solid preparation of aripiprazole.

In the present invention, when the solid particles preparation of aripiprazole is prepared by wet granulation, the said excipients can be selected from any known and widely used excipients in this field, such as fillers. When tablet or capsule of aripiprazole is prepared by wet granulation, the said excipients can be selected from any known and widely used excipient in this field, such as fillers, disintegrants, lubricants and so on. When dry suspension of aripiprazole is prepared by wet granulation, the said excipients can be selected from any known and widely used excipients in this field, such as suspending agents and lubricants. The said fillers can be the fillers that are conventionally used in this preparation field, preferably one or more among lactose, microcrystalline cellulose, pregelatinized starch, starch, mannitol, sucrose and maltitol. The said disintegrants can be the disintegrants that are conventionally used in this preparation field, preferably one or more among carboxymethyl starch sodium, hydroxypropyl cellulose, cross-linked polyvinylpyrrolidone and crosslinked carboxymethylcellulose sodium. The said lubricants can be the lubricants that are conventionally used in this preparation field, preferably one or more among colloidal silica, sodium stearyl fumarate, talcum powder and magnesium stearate. The said suspending agents can be the suspending agents that are conventionally used in this field, preferably one or more among xanthan gum, arabic gum, povidone, tragacanth, sodium alginate, glycerin, sucrose, mannitol, sorbitol, methyl cellulose, hydroxypropyl methyl cellulose, carboxymethyl starch sodium, carboxymethyl cellulose sodium and silicon bentonite. The dosage of the said excipients can be selected according to the conventional knowledge in the present field, the dosage of the said fillers and the water-soluble carriers aforementioned is preferably 70~90% the mass of aripiprazole medicament formulation, which is to say that if the water-soluble carriers are not added before the alkalizer is added, the dosage of the said fillers are 70~90% the mass of aripiprazole medicament formulation, while lithe water-soluble carriers are added, the dosage of the said water-soluble carriers and the said fillers should just satisfy that the sum of the dosage of the said water-soluble carriers and the said fillers is 70~90%. The total dosage of the said disintegrants is preferably 1~10% the mass of aripiprazole medicament formulation, and the total dosage of the said disintegrants here refers to the dosage of the disintegrants used as excipients of wet granulation and the dosage of the disintegrants that are added before the alkalizer. The dosage of the said lubricant is preferably 0.2~3% the mass of aripiprazole medicament formulation. The dosage of the said suspending agents is preferably 85~95% the mass of the dry suspension.

In a preferred embodiment of the present invention, when the solid particles preparations, tablets or capsules of aripiprazole are prepared by wet granulation, the method comprises the following steps: (1) dissolving aripiprazole in aqueous ethanol solution having hydrochloric acid to obtain the medicament having acidic solution; (2) adding water-soluble carrier, antioxidant and alkalizer to get a mixture, and the water-soluble carriers and antioxidants being added before or during the time when the alkalizers are added; (3) caning on wet granulation with the said mixture and the said excipients to obtain the solid particles preparations, or earring on wet granulation and pressing to obtain tablets, or caning on wet granulation and loading capsules to obtain capsules; wherein the alkalizers are sodium hydroxide and/or sodium carbonate; when the said alkalizer is sodium hydroxide, the said alkalizer is added in the form of water solution of sodium hydroxide, the molar ratio of hydrochloric acid to aripiprazole is 0.95~1.1, preferably 1.0~1.05; the molar ratio of alkalizer to hydrochloric acid is 0.99~1.02.

In step (1), the said medicament having acidic solution also contains a surfactant and/or a solubilizer, and the said surfactant and/or solubilizer is preferably one or more among povidone, sodium dodecyl sulfate, poloxamers, Tween 80 and polyoxyethylenated castor oil. The dosage of the said surfactant and/or solubilizer is preferably 0.02~1 times the mass of aripiprazole. The concentration of ethanol in the said medicament having acidic solution is preferably 70 wt % or more, more preferably 80 wt % or more. The said medicament having acidic solution also contains a water-soluble carrier: polyethylene glycol 6000 and hydroxypropyl-β-cyclodextrin.

In step (2), the said mixture also contains a disintegrant, the said disintegrant is added before or during the time when the alkalizer is added. The said disintegrant is preferably sodium carboxymethyl starch and/or cross-linked polyvinylpyrrolidone. The dosage of the said disintegrant is preferably 0.6~0.72 times the mass of aripiprazole. The said water-soluble carrier is preferably one or more among lactose, mannitol, polyethylene glycol 6000 and hydroxypropyl-β-cyclodextrin. The dosage of the said water-soluble carrier is preferably 2~6 times the mass of aripiprazole. The said antioxidant is preferably one or more among sodium bisulfite, sodium sulfite, sodium ascorbate, L-cysteine and sodium thiosulfate. The dosage of the said antioxidant is preferably 1~10% the mass of aripiprazole, more preferably 1~5%. The concentration of the water solution of sodium hydroxide is preferably 10~20 wt %. There is no particular requirement to the order of addition of the said disintegrant, antioxidant and water-soluble carrier. When the alkalizer is sodium hydroxide, it is preferably to add one or more among citric acid, glycine and malic acid before or during the time when the alkalizer is added, and the dosage of which is preferably 0.5~2% the mass of aripiprazole.

In step (3), the said filler is preferably one or more among lactose, microcrystalline cellulose, starch and mannitol, and the total dosage of the said filler and the said water-soluble carrier is 80~90% the mass of the solid particles preparations, tablets or capsules of aripiprazole. The said disintegrant is preferably one or more among sodium carboxymethyl starch, hydroxypropyl cellulose, cross-linked polyvinylpyrrolidone and crosslinked carboxymethylcellulose sodium, whose dosage is preferably 1~10% the mass of tablets or capsules of aripiprazole. The said lubricant is preferably one or more among colloidal silica, sodium stearyl fumarate, talcum powder and magnesium stearate, whose dosage is preferably 0.5~3% the mass of tablets or capsules of aripiprazole.

In a preferred embodiment of the present invention, when the dry suspension of aripiprazole is prepared by wet granulation, the method comprises the following steps: (1) dissolving aripiprazole in an aqueous ethanol solution having hydrochloric acid to obtain the medicament having acidic solution; (2) adding a water-soluble carrier, antioxidant and alkalizer to obtain a mixture, and the water-soluble carrier and antioxidant being added before or during the time when the alkalizer is added; (3) carring on wet granulation with the said mixture and the said excipients to obtain the dry suspension of aripiprazole; wherein the alkalizer is sodium hydroxide and/or sodium carbonate. When the said alkalizer is sodium hydroxide, it is added in the form of aqueous sodium hydroxide solution. The molar ratio of hydrochloric acid to aripiprazole is 0.95~1.1, preferably 1.0~1.05. The molar ratio of alkalizer to hydrochloric acid is 0.99~1.02.

Wherein step (1) and step (2) are as mentioned above, and in step (3), the said suspending agent is preferably one or more among xanthan gum, mannitol and hydroxypropyl methyl cellulose. The dosage of the said suspending agent is preferably 90~96% the mass of the dry suspension. The dosage of the said lubricant is preferably 0.2~0.5% the mass of the dry suspension.

In the present invention, the excipients can be selected according to the prior art when a suspension is prepared, and the said excipients include 5~25% suspending agent, 0~0.5% wetting agent, 0~0.3% preservative, 0~3% corrective agent and solvent, the percentage is mass percentage relative to the suspension. The said suspending agent is preferably selected from one or more among xanthan gum, arabic gum, povidone, tragacanth, sodium alginate, glycerin, sucrose, mannitol, sorbitol, methyl cellulose, hydroxypropyl methyl cellulose, carboxymethyl starch sodium, carboxymethyl cellulose sodium and silicon bentonite. The said wetting agent is preferably selected from one or more among Tween 80, polyoxyethylene aliphatic alcohol ether (Brij), polyoxyethylene fatty acid (Myrij), poloxamer and sodium dodecyl sulfate. The said solvent is usually water or the mixture of water and alcohol. The said alcohol is generally one or more among propylene glycol, benzyl alcohol and ethanol. The dosage of the solvent is to complement the weight percent of the suspension up to 100%. The said suspension also includes preservative and/or corrective agent, and the preservative is preferably selected from one or more among benzoic acid, sodium benzoate, propyl hydroxybenzoate, sodium propyl hydroxybenzoate, methyl hydroxybenzoate and sodium methyl hydroxybenzoate, sorbic acid and so on, the corrective agent is preferably selected from one or more among aspartame, stevia, flavor and so on.

In the present invention, the method of preparing the said suspension is mixing the said medicament having acidic solution with the alkalizer, and preferably is carried out concretely according to any one of the following methods: method (1) uniformly mixing the medicament having acidic solution with the alkalizer or the alkalizer-containing solution, and then mixing them with the suspending agent solution; method (2) uniformly mixing the medicament having acidic solution with the water-soluble carrier and/or disintegrant, and then uniformly mixing them with the alkalizer or the alkalizer-containing solution, further mixing them with the suspending agent solution; method (3) uniformly mixing the medicament having acidic solution with the water-soluble carrier and/or disintegrant, and also with the suspending agent solution, and then mixing them with the alkalizer or the alkalizer-containing solution. Wherein the said suspending agent solution is obtained by mixing the other excipients contained in the said suspending agent with the suspending agent. In the process of preparation, the conventional steps for preparing a suspension can also be used in the present field, such as proceeding the dispersing treatment with a colloid mill, homogenizer and so on.

In a preferred embodiment of the present invention, the method of preparing a suspension comprises the following steps: (1) dissolving aripiprazole in a solution having an acidifier so as to obtain a medicament having acidic solution; (2) adding the said water-soluble carrier, the said antioxidant and the said alkalizer to obtain a mixture, and the water-soluble carrier and antioxidant being added before or during the time when the alkalizer is added; (3) mixing the mixture with the said suspending agent solution. Wherein, the said alkalizer is sodium hydroxide, and the said sodium hydroxide is added in the form of aqueous sodium hydroxide solution with a concentration of 5~20 wt %. The said acidifier is hydrochloric acid and/or lactic acid, and the molar ratio of the hydrochloric acid to aripiprazole is preferably 1.0~1.1, the molar ratio of the said lactic acid to aripiprazole is generally 1.8~2.5, preferably 2~2.1. The molar ratio of the alkalizer to hydrochloric acid is 0.99~1.02. In step (1), the solvent of the medicament having acidic solution is one or more among the following alcohols, or the aqueous solution of the following alcohols: ethanol, propylene glycol, glycerol and benzyl alcohol.

Wherein step (1), the said medicament having acidic solution preferably contains a surfactant and/or a solubilizer. The said surfactant and/or solubilizer is preferably one or more among povidone, Tween 80 and poloxamer. The dosage of the said surfactant and/or solubilizer is preferably 0.25~2.5 times the mass of aripiprazole. The concentration of alcohol in the said aqueous alcohol solution is preferably 70 wt % or more. The said medicament having acidic solution also preferably contains a water-soluble carrier: polyethylene glycol 6000. In step (2), the said water-soluble carrier is preferably one or more among sucrose, mannitol and polyethylene glycol 6000. The total dosage of the said water-soluble carrier is preferably 7~10 times the mass of aripiprazole. The said antioxidant is preferably one or more among sodium bisulfite, sodium sulfite, sodium ascorbate, L-cysteine and sodium thiosulfate. The dosage of the said antioxidant is preferably 10~100% the mass of aripiprazole. In step (3), the said suspending agent is preferably one or more among xanthan gum, hydroxypropyl methyl cellulose, sucrose and sodium carboxymethyl cellulose. The dosage of the said suspending agent is preferably 1~15.5% the mass of the suspension.

In the preparation method of the present invention, the particle size of aripiprazole formulation can be controlled by adjusting the ratio in prescription and the conditions of operation. The said ratio in prescription refers to the ratio of solvents used for preparing the medicament having acidic solution particularly, and as well as the species and ratios of water-soluble carriers and other reagents of the solid dispersion added in the medicament having acidic solution before the alkalizer is added. The particle size of aripiprazole can also be affected by the stirring speed, the method of adding an alkalizer and so on. Therefore, the preparation method disclosed in the invention can adjust the particle size of aripiprazole according to the requirement, which has also provided an effective method of ensuring and controlling the dissolution characteristic of preparation. In the present invention, when the solvent is aqueous ethanol solution, the particle size would be affected by the concentration of the solvent, and the size will be the smallest when the concentration reaches 95%. The regular between the particle size of aripiprazole and the stirring speed is as follows: with the increase of the stirring speed, the particle size is presented an increasing tendency. When one of the surfactant, solubilizer and water-soluble carrier is added into the medicament having acidic solution, the particle size will be reduced with the increasing of the dosage of said excipients. When at least two of the surfactant, solubilizer and water-soluble carrier are added into the medicament having acidic solution and under the condition that the dosage of one excipient is fixed, the particle size will be reduced with the increase of the dosage of the other excipient. When aripiprazole:lactose is 1:6 and aripiprazole: Tween 80 (or poloxamer or sodium dodecyl sulfate) is 1:0.2, the effect of reducing the particle size realized by adding Tween-80 is better than poloxamer, and poloxamer is better than sodium dodecyl sulfate. When one of mannitol, lactose, maltitol and sucrose is added into the medicament having acidic solution, the particle size will be reduced with the increase of the dosage of the said excipient.

Further, the present invention has also provided an aripiprazole medicament formulation produced by the above-mentioned method.

In the present invention, the mentioned optimized conditions can be optionally combined based on the general knowledge in this field to obtain preferred embodiments.

In the present invention, the used reagents and materials can be commercially available.

The positive effects of the present invention are:

(1) The amount of related substances is significantly decreased in the aripiprazole medicament formulation obtained by the preparation method in this invention, and the formulation also possesses great solubility and stability, high bioavailability, small individual differences. (2) The insoluble aripiprazole is highly dispersed in suitable excipients during the preparation of the invention, which has changed the surface properties of microcrystalline, improved the wettability and content uniformity of the insoluble drug. (3) The preparation method of the invention combines the microcrystalline of the insoluble medicament and the process of dispersion with the granulation, which realizes simple operation, low cost, no special equipment requirement and easy application to industrialization. (4) The preparation method of the invention eliminates the influence of the form of crude drug on quality of preparation, and avoids the defects of serious pollution, great lost and high security risks caused by the pretreatment of aripiprazole.

DETAILED DESCRIPTION OF THE PREFERRED EMBODIMENT

Then the present invention is further illustrated by the following embodiments, but is not limited by the following embodiments. In the following embodiments, the experimental methods without specific conditions, can be carried on by conventional conditions or the conditions recommended by manufacturers.

In the following embodiments, dosage specification counts as the dosage of aripiprazole, for example, 5 mg/tablet refers to 5 mg aripiprazole per tablet. Dosage unit is gram, and percentage refers to mass percentage. The stirring linear speed without specified when water-soluble carrier and alkalizer are added in the medicament having acidic solution is 160 m/min.

In the embodiments, the solvent of medicament having acidic solution is the solvent contained in the prepared medicament having acidic solution, and the solvent refers to all of the solvents added during the preparation of a medicament preparation. Take example 1 for example, the preparation of the medicament having acidic solution is: mixing povidone, 15.2 g anhydrous ethanol, 4.3 g 10% aqueous hydrochloric acid solution and 5 g aripiprazole to prepare the medicament having acidic solution. The solvent of medicament having acidic solution is aqueous ethanol solution. The mass of the aqueous ethanol solution is: 15.2 g anhydrous ethanol+3.87 g water (4.3−4.3*10%)=19.1 g. The concentration of the aqueous ethanol solution is: (15.2/19.1)*100%=80%. The mass of the solvent is: 19.2 g the solvent of medicament having acidic solution plus the water contained in aqueous sodium hydroxide solution (2.36−2.36*20%)=19.2+1.888=21.0 g, and the concentration of the solvent is (15.2/21)*100%=72%.

Hereinafter, [1] refers to the percentage of aripiprazole counting for the mass of dry material of wet granulation. [2] refers to the percentage of the solvent counting for the mass of dry material of wet granulation. [3] refers to the percentage of aripiprazole counting for the mass of the suspension.

Comparison Examples 1~2 and Examples 1~2

Prescription and Preparation Method of Aripiprazole Granules (Unit: Gram)

|  | Comparison Example 1 | Comparison Example 2 | Example 1 | Example 2 |
|---|---|---|---|---|
| Drug | Aripiprazole 5 g (2.4%[1], grain diameter D [4, 3] 92.7 micron) | Aripiprazole 5 g (2.4%[1], grain diameter D [4, 3] 26.3 micron) | Aripiprazole 5 g (2.4%[1], without pretreatment) | Aripiprazole 5 g (2.4%[1], without pretreatment) |
| Excipient | Lactose 200 g, Povidone K-30 2.5 g | Lactose 200 g, Povidone K-30 2.5 g | Lactose 200 g, Povidone K-30 2.5 g, Sodium Hydrogen Sulfite 0.1 g | Lactose 172.5 g, Mannitol 25 g, Povidone K-30 5 g, Sodium Hydrogen Sulfite 0.1 g |
| Medicament having acidic solution | — | — | 80% Aqueous ethanol solution 19.1 g | 91% Aqueous ethanol solution 19.0 g |
| Solvent | 75% Aqueous ethanol solution 20 g (9.6%[2]) | 75% Aqueous ethanol solution 20 g (9.6%[2]) | 72% Aqueous ethanol solution 21.0 g (10.1%[2]) | 83% Aqueous ethanol solution 20.9 g (10.0%[2]) |
| Acidifier | — | — | 10% Aqueous hydrochloric acid solution 4.3 g (molar ratio of it to aripiprazole is 1.05) | 36% Hydrochloric acid 1.18 g (molar ratio of it to aripiprazole is 1.05) |
| Alkalizer | — | — | 20% Aqueous Sodium hydroxide solution 2.36 g (molar ratio of it to hydrochloric acid is 1.0) | 20% Aqueous sodium hydroxide solution 2.33 g (molar ratio of it to hydrochloric acid is 1.0) |
| Preparation Technology | Grind aripiprazole by a universal pulverizer and then make it pass through 100 mesh sieve; uniformly mix it with lactose; povidone in 75% | Carry on micronization treatment with aripiprazole, uniformly mix it with lactose; povidone in 75% aqueous ethanol solution is added, | Mix povidone, 15.2 g anhydrous ethanol, aqueous hydrochloric acid solution and aripiprazole to prepare medicament having acidic solution; add sodium hydrogen sulfite; add 15% amount of lactose when stirring; then | Mix povidone, 18.24 g 95% ethanol, hydrochloric acid and aripiprazole to prepare medicament having acidic solution, add sodium hydrogen sulfite; add mannitol when stirring; then add aqueous sodium hydroxide solution |

-continued

| | Comparison Example 1 | Comparison Example 2 | Example 1 | Example 2 |
|---|---|---|---|---|
| | aqueous ethanol solution is added, stir and granulation; finish granule after drying wet granules. | stir and granulation; finish granule after drying wet granules. | add aqueous sodium hydroxide solution quickly when stirring. Add the above mixture into the rest lactose to carry out stirring granulation; finish granule after drying wet granules. | dropwise when stirring. Add the above mixture into the lactose to carry out stirring granulation; finish granule after drying wet granules. |

Contrastive Examples 3~4 and Examples 3~4

Prescription and Preparation Method of Aripiprazole Tablets (Unit: Gram)

| | Contrastive Example 3 | Contrastive Example 4 | Example 3 | Example 4 |
|---|---|---|---|---|
| Drug | Aripiprazole 5 g (4.2%[1], grain diameter D[4, 3] 92 micron) | Aripiprazole 5 g (4.2%[1], grain diameter D[4, 3] 25 micron) | Aripiprazole 5 g (4.2%[1], without pretreatment) | Aripiprazole 5 g (4.2%[1], without pretreatment) |
| Excipient | Lactose 75 g, Povidone K-30 2.5 g, Microcrystalline Cellulose 30 g, Carboxymethyl Starch Sodium 5 g, Magnesium Stearate 0.9 g | Lactose 75 g, Povidone K-30 2.5 g, Microcrystalline Cellulose 30 g, Carboxymethyl Starch Sodium 5 g, Magnesium Stearate 0.9 g | Lactose 75 g, Povidone K-30 2.5 g, Microcrystalline Cellulose 30 g, Sodium Hydrogen Sulfite 0.1 g, Carboxymethyl Starch Sodium 5 g, Magnesium Stearate 0.9 g | Mannitol 72.5 g, Povidone K-30 5 g, Microcrystalline Cellulose 30 g, Sodium Hydrogen Sulfite 0.1 g, Carboxymethyl Starch Sodium 5 g, Magnesium Stearate 0.9 g |
| Medicament having acidic solution | — | — | 80% Aqueous ethanol solution 19.1 g | 91% Aqueous ethanol solution 19.0 g |
| Solvent | 75% Aqueous ethanol solution 20 g (16.9%[2]) | 75% Aqueous ethanol solution 20 g (16.9%[2]) | 65% Aqueous ethanol solution 23.3 g (19.5%[2]) | 75% Aqueous ethanol solution 23.2 g (19.5%[2]) |
| Acidifier | — | — | 10% Aqueous hydrochloric acid solution 4.3 g (molar ratio of it to aripiprazole is 1.05) | 36% Hydrochloric acid 1.18 g (molar ratio of it to aripiprazole is 1.05) |
| Alkalizer | — | — | 10% Aqueous sodium hydroxide solution 4.7 g (molar ratio of it to hydrochloric acid is 1.0) | 10% Aqueous sodium hydroxide solution 4.7 g (molar ratio of it to hydrochloric acid is 1.0) |
| Preparation Technology | Mix aripiprazole with lactose, microcrystalline cellulose uniformly; add povidone, aqueous ethanol solution to carry out stirring granulation; finish granule after drying wet granules; add magnesium stearate and carboxymethyl starch sodium, uniformly mix and press. | Mix aripiprazole with lactose, microcrystalline cellulose uniformly; add povidone, aqueous ethanol solution to carry out stirring granulation; finish granule after drying wet granules; add magnesium stearate and carboxymethyl starch sodium, uniformly mix and press. | Mix povidone, 15.2 g anhydrous ethanol, aqueous hydrochloric acid and aripiprazole to prepare medicament having acidic solution; add sodium hydrogen sulfite; add 40% amount of lactose when stirring, then add aqueous sodium hydroxide solution quickly when stirring to get mixture. Add the mixture to the mixed powder of the rest lactose and microcrystalline cellulose to carry out stirring granulation; finish granule after drying wet granules. Add magnesium stearate and carboxymethyl starch sodium, uniformly mix and press. | Mix povidone, 18.24 g 95% ethanol, hydrochloric acid and aripiprazole to prepare medicament having acidic solution; add sodium hydrogen sulfite; add 35% amount of mannitol when stirring; then add aqueous sodium hydroxide solution dropwise when stirring to get mixture. Add the mixture to the mixed powder of the rest mannitol and microcrystalline cellulose to carry out stirring granulation; finish granule after drying wet granules. Add magnesium stearate and carboxymethyl starch sodium, uniformly mix and press. |

Examples 5 and 6

Prescription and Preparation Method of Aripiprazole Tablets (5 Mg/Tablet) (Unit: Gram)

| | Example 5 | Example 6 |
|---|---|---|
| Drug | Aripiprazole 5 g (4.1%[1], without pretreatment) | Aripiprazole 5 g (4.1%[1], without pretreatment) |
| Excipient | Lactose 70 g, Microcrystalline Cellulose 20 g, Starch 20 g, Povidone K-30 2.5 g, Sodium | Lactose 70 g, Microcrystalline Cellulose 20 g, Starch 20 g, PovidoneK-30 2.5 g, Sodium |

-continued

|  | Example 5 | Example 6 |
| --- | --- | --- |
|  | Hydrogen Sulfite 0.5 g, Magnesium Stearate 0.7 g, Cross-linked polyvinylpyrrolidone 2 g | Hydrogen Sulfite 0.5 g, Magnesium Stearate 0.7 g, Cross-linked polyvinylpyrrolidone 2 g |
| Medicament having acidic solution | 96% Aqueous ethanol solution 15.7 g | 77% Aqueous ethanol solution 15.6 g |
| Solvent | 76% Aqueous ethanol solution 19.7 g (16.2%[2]) | 61% Aqueous ethanol solution 19.5 g (16.1%[2]) |
| Acidifier | 36% Hydrochloric acid 1.1 g (molar ratio of it to aripiprazole is 0.98) | 10% Aqueous hydrochloric acid solution 3.96 g (molar ratio of it to aripiprazole is 0.98) |
| Alkalizer | 10% Aqueous sodium hydroxide solution 4.4 g (molar ratio of it to hydrochloric acid is 1.01) | 10% Aqueous sodium hydroxide solution 4.4 g (molar ratio of it to hydrochloric acid is 1.01) |
| Preparation Technology | Mix povidone, 15 g anhydrous ethanol, hydrochloric acid and aripiprazole to prepare medicament having acidic solution; add 20% amount of lactose when stirring; then add sodium hydrogen sulfite and aqueous sodium hydroxide solution when stirring to get mixture. Add the mixture into the mixed powder of the rest 80% amount of lactose, starch and microcrystalline cellulose to carry out stirring granulation; finish granule after drying wet granules; add magnesium stearate and cross-linked polyvinyl-pyrrolidone, uniformly mix and press. | Mix povidone, 12 g anhydrous ethanol, aqueous hydrochloric acid solution and aripiprazole to prepare medicament having acidic solution; add 20% amount of lactose when stirring; then add sodium hydrogen sulfite and aqueous sodium hydroxide solution when stirring to get mixture. Add the mixture into the mixed powder of the rest 80% amount of lactose, starch and microcrystalline cellulose to carry out stirring granulation; finish granule after drying wet granules; add magnesium stearate and cross-linked polyvinylpyrrolidone, uniformly mix and press. |

Examples 7 and 8

Prescription and Preparation Method of Aripiprazole Tablets (5 Mg/Tablet) (Unit: Gram)

|  | Example 7 | Example 8 |
| --- | --- | --- |
| Drug | Aripiprazole 5 g (4.2%[1], without pretreatment) | Aripiprazole 5 g (4.1%[1], without pretreatment) |
| Excipient | Lactose 60 g, Microcrystalline Cellulose 20 g, Starch 25 g, Poloxamer188 0.5 g, Carboxymethyl Starch Sodium 6 g, L-cysteine 0.1 g, Magnesium Stearate 0.8 g | Lactose 75 g, Microcrystalline Cellulose 30 g, Povidone K-30 2.5 g,, Carboxymethyl Starch Sodium 6 g, Sodium Hydrogen Sulfite 0.1 g, Magnesium Stearate 0.8 g |
| Medicament having acidic solution | 73% Aqueous ethanol solution 15.6 g | 76% Aqueous ethanol solution 15.7 g |
| Solvent | 58% Aqueous ethanol solution 19.6 g (16.5%[2]) | 61% Aqueous ethanol solution (16.1%[2]) |
| Acidifier | 10% Hydrochloric acid 4 g (molar ratio of it to aripiprazole is 0.99) | 10% Aqueous hydrochloric acid solution 3.4 g (molar ratio of it to aripiprazole is 0.84) Citric Acid Monohydrate 0.35 g (molar ratio of it to aripiprazole is 0.15) |
| Alkalizer | 10% Aqueous Sodium hydroxide solution 4.4 g (molar ratio of it to hydrochloric acid is 1.0) | 10% Aqueous Sodium hydroxide solution 4.35 g (molar ratio of it to the mixed acid is 0.99) |
| Preparation Technology | Mix 12 g 95% ethanol, aqueous hydrochloric acid solution, poloxamer and aripiprazole to prepare medicament having acidic solution; add L-cysteine, 50% amount of carboxymethyl starch sodium and 40% amount of lactose when stirring; add aqueous sodium hydroxide solution when stirring to get mixture. Add the mixture into the mixed powder of 60% amount of lactose, starch and microcrystalline cellulose to carry out stirring granulation; finish granule after drying wet granules; add magnesium stearate and 50% amount of carboxymethyl starch sodium, uniformly mix and press. | Mix 12.6 g 95% ethanol, aqueous hydrochloric acid solution, citric acid monohydrate and aripiprazole to prepare medicament having acidic solution; add sodium hydrogen sulfite and 30% amount of lactose when stirring, then add aqueous sodium hydroxide solution when stirring to get mixture. Add the mixture to the mixed powder of 70% amount of lactose, 50% amount of carboxymethyl starch sodium and microcrystalline cellulose to carry out stirring granulation; finish granule after drying wet granules; add magnesium stearate and 50% amount of carboxymethyl starch sodium, uniformly mix and press. |

Examples 9 and 10

Prescription and Preparation Method of Aripiprazole Tablets (5 Mg/Tablet) (Unit: Grain)

|  | Example 9 | Example 10 |
| --- | --- | --- |
| Drug | Aripiprazole 5 g (4.5%[1], without pretreatment) | Aripiprazole 5 g (4.5%[1], without pretreatment) |

-continued

|  | Example 9 | Example 10 |
|---|---|---|
| Excipient | Lactose 70 g, Microcrystalline Cellulose 30 g, Povidone K-30 1.5 g, Sodium Sulfite 0.05 g, Citric Acid Monohydrate 0.05 g, Sodium Dodecyl Sulfate 0.1 g, Carboxymethyl Starch Sodium 4 g, Magnesium Stearate 0.6 g | Lactose 70 g, Microcrystalline Cellulose 30 g, Povidone K-30 1.5 g, Sodium Sulfite 0.05 g, Citric Acid Monohydrate 0.05 g, Sodium Dodecyl Sulfate 0.1 g, Carboxymethyl Starch Sodium 4 g, Magnesium Stearate 0.6 g |
| Medicament having acidic solution | 76% Aqueous ethanol solution 18.7 g | 76% Aqueous ethanol solution 18.7 g |
| Solvent | 63% Aqueous ethanol solution 22.7 g (20.3%[2]) | 63% Aqueous ethanol solution 22.7 g (20.3%[2]) |
| Acidifier | 10% Aqueous hydrochloric acid solution 4.1 g (molar ratio of it to aripiprazole is 1.01) | 10% Aqueous hydrochloric acid solution 4.1 g (molar ratio of it to aripiprazole is 1.01) |
| Alkalizer | 10% Aqueous Sodium hydroxide solution 4.5 g (molar ratio of it to hydrochloric acid is 1.0) | 10% Aqueous sodium hydroxide solution 4.5 g (molar ratio of it to hydrochloric acid is 1.0) |
| Preparation Technology | Mix 15 g 95% ethanol, sodium dodecyl sulfate, povidone, aqueous hydrochloric acid solution and aripiprazole to prepare medicament having acidic solution; add sodium sulfite, citric acid monohydrate and 20% amount of lactose when stirring; then add aqueous sodium hydroxide solution when stirring to get mixture. Add the mixture to the mixed powder of 80% amount of lactose and microcrystalline cellulose to carry out stirring granulation; finish granule after drying wet granules; add magnesium stearate and carboxymethyl starch sodium, uniformly mix and press. | Mix 15 g 95% ethanol, sodium dodecyl sulfate, povidone, aqueous hydrochloric acid solution and aripiprazole to prepare medicament having acidic solution; add sodium sulfite, citric acid monohydrate and 50% amount of lactose when stirring; then add aqueous sodium hydroxide solution when stirring to get mixture. Add the mixture into the mixed powder of 50% amount of lactose and microcrystalline cellulose to carry out stirring granulation; finish granule after drying wet granules; add magnesium stearate and carboxymethyl starch sodium, uniformly mix and press. |

Examples 11

Prescription and Preparation Method of Aripiprazole Tablets (10 Mg/Tablet) (Unit: Gram)

| Drug | Aripiprazole 10 g (7.8%[1], without pretreatment) |
|---|---|
| Excipient | Lactose 70 g, Povidone K-30 5 g, Starch 37 g, Tween-80 0.1 g, Sodium Hydrogen Sulfite 0.5 g, DL Malic Acid 0.1 g, Carboxymethyl Starch Sodium 3, Colloidal Silica 0.2 g, Sodium Stearyl Fumarate 0.8 g |
| Medicament having acidic solution | 94% Ethanol 26.5 g |
| Solvent | 83% Aqueous ethanol solution 30.1 g (23.4%[2]) |
| Acidifier | 36% Hydrochloric acid 2.3 g (molar ratio of it to aripiprazole is 1.02) |
| Alkalizer | 20% Aqueous sodium hydroxide solution 4.5 g (molar ratio of it to hydrochloric acid is 0.99) |
| Preparation Technology | Mix 25 g anhydrous ethanol, Tween-80, povidone, hydrochloric acid and aripiprazole to prepare medicament having acidic solution; stir when adding malic acid, sodium hydrogen sulfite and 40% amount of lactose; then add aqueous sodium hydroxide solution when stirring to get mixture. Add the mixture to the mixed powder of 60% amount of lactose and starch to carry out stirring granulation; finish granule after drying wet granules; add colloidal silica, carboxymethyl starch sodium, sodium stearyl fumarate, uniformly mix and press. |

Examples 12

Prescription and Preparation Method of Aripiprazole Tablets (5 Mg/Tablet) (Unit: Gram)

| Drug | Aripiprazole 5 g (4.1%[1], without pretreatment) |
|---|---|
| Excipient | Lactose 60 g, Microcrystalline Cellulose 40 g, Polyethylene Glycol 6000 10 g, Polyoxyethylated Castor Oil 0.1 g, Carboxymethyl Starch Sodium 6 g, Sodium Sulfite 0.2 g, Citric Acid Monohydrate 0.06 g, Magnesium Stearate 0.8 g |
| Medicament having acidic solution | 72% Aqueous ethanol solution 15.68 g |
| Solvent | 58% Aqueous ethanol solution 19.8 g (16.1%[2]) |
| Acidifier | 10% Aqueous hydrochloric acid solution 4.2 g (molar ratio of it to aripiprazole is 1.03) |
| Alkalizer | 10% Aqueous Sodium hydroxide solution 4.5 g (molar ratio of it to hydrochloric acid is 0.98) |
| Preparation Technology | Mix 12 g 95% ethanol, polyethylene glycol, polyoxyethylated castor oil, aqueous hydrochloric acid solution and aripiprazole to prepare medicament having acidic solution; add sodium sulfite, citric acid monohydrate, 60% amount of carboxymethyl starch sodium and 50% amount of lactose when stirring; then add aqueous sodium hydroxide solution when stirring to get mixture. Add the mixture to the mixed powder of 50% amount of lactose and microcrystalline cellulose to carry out stirring granulation; finish granule after drying wet granules; add 40% amount of carboxymethyl starch sodium and magnesium stearate, uniformly mix and press. |

Examples 13

Prescription and Preparation Method of Aripiprazole Tablets (10 Mg/Tablet) (Unit: Gram)

| Drug | Aripiprazole 10 g (6.8%[1], without pretreatment) |
|---|---|
| Excipient | Lactose 65 g, Microcrystalline Cellulose 65 g, Povidone K-30 2 g, Sodium Hydrogen Sulfite 0.2 g, Citric Acid Monohydrate 0.06 g, Carboxymethyl Starch Sodium 3 g, Magnesium Stearate 0.8 g |
| Medicament having acidic solution | 96% Aqueous ethanol solution 31.41 g |
| Solvent | 76% Aqueous ethanol solution 39.2 g (26.5%[2]) |
| Acidifier | 36% Hydrochloric acid 2.2 g (molar ratio of it to aripiprazole is 0.98) |
| Alkalizer | 10% Aqueous Sodium hydroxide solution 8.6 g (molar ratio of it to hydrochloric acid is 0.99) |

-continued

| | |
|---|---|
| Preparation Technology | Mix 30 g anhydrous ethanol, povidone, hydrochloric acid and aripiprazole to prepare medicament having acidic solution; add citric acid monohydrate, sodium hydrogen sulfite and aqueous sodium hydroxide solution when stirring; add 35% amount of lactose when stirring to get mixture. Add the mixture to the mixed powder of 65% amount of lactose and microcrystalline cellulose to carry out stirring granulation; finish granule after drying wet granules; add carboxymethyl starch sodium and magnesium stearate, uniformly mix and press. |

Example 14

Prescription and Preparation Method of Aripiprazole Capsules (10 Mg/Tablet)

Make the granules (including the carboxymethyl starch sodium and magnesium stearate) before pressing prepared by Example 13 pass through 30 mesh sieve and mix uniformly, then load into capsules.

Examples 15

Prescription and Preparation Method of Aripiprazole Tablets (5 Mg/Tablet) (Unit: Gram)

| | |
|---|---|
| Drug | Aripiprazole 5 g (4.1%[1], without pretreatment) |
| Excipient | Mannitol 60 g, Microcrystalline Cellulose 40 g, Tween 80 0.2 g, Polyethylene Glycol 6000 10 g, Carboxymethyl Starch Sodium 6 g, L-cysteine 0.2 g, Magnesium Stearate 0.8 g |
| Medicament having acidic solution | 71% Aqueous ethanol solution 16.1 g |
| Solvent | 58% Aqueous ethanol solution 19.7 g (15.9%[2]) |
| Acidifier | 10% Aqueous hydrochloric acid solution 4.5 g (molar ratio of it to aripiprazole is 1.11) |
| Alkalizer | 10% Aqueous Sodium hydroxide solution 4 g (molar ratio of it to hydrochloric acid is 0.81) Sodium carbonate 0.25 g (molar ratio of it to hydrochloric acid is 0.19) |
| Preparation Technology | Mix 12 g 95% ethanol, polyethylene glycol, Tween 80, aqueous hydrochloric acid solution and aripiprazole to prepare medicament having acidic solution; add L-cysteine, 60% amount of carboxymethyl starch sodium and 40% amount of mannitol when stirring; add aqueous sodium hydroxide solution and the mixed powder of sodium carbonate and 10% amount of mannitol when stirring to get mixture. Add the mixture to the mixed powder of 50% amount of mannitol and microcrystalline cellulose to carry out stirring granulation; finish granule after drying wet granules; add 40% amount of carboxymethyl starch sodium and magnesium stearate, uniformly mix and press. |

Example 16

Prescription and Preparation Method of Aripiprazole Tablets (20 Mg/Tablet) (Unit: Gram)

| | |
|---|---|
| Drug | Aripiprazole 20 g (15.0%[1], without pretreatment) |
| Excipient | Lactose 60 g, Microcrystalline Cellulose 40 g, Carboxymethyl Starch Sodium 6 g, Sodium Sulfite 0.2 g, Povidone K-30 3 g, Magnesium Stearate 0.8 g, Colloidal Silica 0.3 g |
| Medicament having acidic solution | 78% Aqueous ethanol solution 73.1 g |
| Solvent | 57% Aqueous ethanol solution 100.2 g (74.7%[2]) |
| Acidifier | 10% Aqueous hydrochloric acid solution 14.6 g (molar ratio of it to aripiprazole is 0.90) Citric Acid Monohydrate 0.54 g (molar ratio of it to aripiprazole is 0.05) |
| Alkalizer | 10% Aqueous Sodium hydroxide solution 17.9 g (molar ratio of it to the acidifier is 1.0) |
| Preparation Technology | Mix 60 g 95% ethanol, aqueous hydrochloric acid solution, povidone, citric acid monohydrate and aripiprazole to prepare medicament having acidic solution; add sodium sulfite and ⅓ amount of lactose when stirring; add aqueous sodium hydroxide solution when stirring; then add 11 g water and stir uniformly to make granulating liquid. Mix ⅔ amount of lactose, microcrystalline cellulose and 60% amount of carboxymethyl starch sodium uniformly and add them into a multi-functional fluidized spray granulator, spray granulating liquid on the above-mentioned mixed excipients by a peristaltic pump to granulation; add magnesium stearate, colloidal silica and 40% amount of carboxymethyl starch sodium to the prepared granules, uniformly mix and then press. |

Example 17

Aripiprazole Capsules (10 Mg/Tablet) (Unit: Gram)

Make the granules (including magnesium stearate, colloidal silica and 40% amount of carboxymethyl starch sodium) before pressing prepared by Example 16 pass through 30 mesh sieve and uniformly mix, then load into capsules.

Example 18

Aripiprazole Suspension (1 Mg/Gram)

| | |
|---|---|
| Drug | Aripiprazole 2 g (0.1%[3], without pretreatment) |
| Excipient | Sucrose 120 g, Sodium Hydrogen Sulfite 2 g, Polyethylene Glycol 6000 2 g Sodium Benzoate 2 g, Hydroxypropyl Methyl Cellulose 100 g, Orange Flavor 2 g |
| Medicament having acidic solution | 73% Aqueous ethanol solution 6.5 g, Glycerin 2 g |
| Solvent | 95% Ethanol 5 g, Glycerin 2 g, Water about 1759 g |
| Acidifier | 10% Aqueous hydrochloric acid solution 1.7 g (molar ratio of it to aripiprazole is 1.05) |
| Alkalizer | 5% Aqueous Sodium hydroxide solution 3.75 g (molar ratio of it to hydrochloric acid is 1.0) |
| Preparation Technology | Disperse hydroxypropyl methyl cellulose with 80° C. hot water, add water until the mass reaches 1000 g and stir to dissolve; then add 90% amount of sucrose, sodium benzoate and orange flavor, stir to dissolve, get the mixture of hydroxypropyl methyl cellulose. Mix 5 g 95% ethanol, glycerin, aqueous hydrochloric acid solution, polyethylene glycol 6000 and aripiprazole to prepare medicament having acidic solution; add sodium hydrogen sulfite and 10% amount of sucrose when stirring, add aqueous sodium hydroxide solution dropwise when stirring. Add the mixture of hydroxypropyl methyl cellulose when stirring; finally add water until the total mass reaches 2000 g and uniformly stir. |

Example 19

Suspension (0.5 Mg/Gram)

| | |
|---|---|
| Drug | Aripiprazole 5 g (0.5%[3], without pretreatment) |
| Excipient | Mannitol 30 g, Povidone K30 2 g, Sodium Hydrogen Sulfite 0.5 g, Poloxamer188 5 g, Xanthan Gum 50 g, Sodium Propylparaben 2 g, Aspartame10 g, Flavors 2 g |
| Medicament having acidic solution | 80% Aqueous propylene glycol solution 23.8 g |
| Solvent | Propylene glycol 20 g, Water about 865 g |
| Acidifier | 10% Aqueous hydrochloric acid solution 4.2 g (molar ratio of it to aripiprazole is 1.04) |
| Alkalizer | 10% Aqueous sodium hydroxide solution 4.6 g (molar ratio of it to hydrochloric acid is 1.0) |
| Preparation Technology | Mix xanthan gum, Sodium Propylparaben, aspartame, flavors and 500 g water to prepare the mixture of xanthan gum. Mix propylene glycol, aqueous hydrochloric acid solution, poloxamer, Povidone K30 and aripiprazole to prepare medicament having acidic solution; add mannitol when stirring, add aqueous sodium hydroxide solution and sodium hydrogen sulfite dropwise when stirring. Add the mixture of xanthan gum when stirring; finally add water until the total mass reaches 1000 g. |

Example 20

Aripiprazole Suspension (1 Mg/Gram)

| | |
|---|---|
| Drug | Aripiprazole 2 g (0.2%[3], without pretreatment) |
| Excipient | Sucrose 156 g, Sodium Hydrogen Sulfite 1 g, Tween 80 1 g, Povidone K30 4 g, Sodium Benzoate 1 g, Hydroxypropyl Methyl Cellulose 50 g, Orange Flavor 2 g |
| Medicament having acidic solution | Propylene glycol 6 g |
| Solvent | 71% Aqueous propylene glycol solution 11.2 g, Water about 778 g |
| Acidifier | DL-Lactic acid 0.81 g (molar ratio of it to aripiprazole is 2.0) |
| Alkalizer | 10% Aqueous sodium hydroxide solution 3.56 g (molar ratio of it to lactic acid is 1.0) |
| Preparation Technology | Disperse hydroxypropyl methyl cellulose with 80° C. hot water, add water until the mass reaches 500 g and stir to dissolve; then add 95% amount of sucrose, sodium benzoate and orange flavor, stir to dissolve, to get the mixture of hydroxypropyl methyl cellulose. Mix propylene glycol, lactic acid, Tween 80, povidone and aripiprazole to prepare medicament having acidic solution; add sodium hydrogen sulfite and 5% amount of sucrose when stirring, add aqueous sodium hydroxide solution dropwise when stirring, add the mixture of hydroxypropyl methyl cellulose when stirring; finally add water until the total mass reaches 1000 g. |

Example 21

Aripiprazole Dry Suspension (20 Mg/Gram)

| | |
|---|---|
| Drug | Aripiprazole 5 g (without pretreatment) |
| Excipient | Mannitol 50 g, Povidone K-30 2 g, Hydroxypropyl Methyl Cellulose 100 g, Xanthan Gum 90 g, Tween 80 0.5 g, Sodium Sulfite 0.1 g, Colloidal Silica 0.5 g |
| Medicament having acidic solution | 96% Aqueous ethanol solution16.6 g |
| Solvent | 77% Ethanol 20.7 g |
| Acidifier | 36% Aqueous hydrochloric acid solution 1 g (molar ratio of it to aripiprazole is 0.88) Citric Acid Monohydrate 0.28 g (molar ratio of it to aripiprazole is 0.12) |
| Alkalizer | 10% Aqueous Sodium hydroxide solution 4.5 g (molar ratio of it to the acidifier is 1.0) |
| Preparation Technology | Mix povidone, 16 g anhydrous ethanol, hydrochloric acid, citric acid monohydrate, Tween80 and aripiprazole to prepare medicament having acidic solution; add sodium sulfite and 40% amount of mannitol when stirring; then add aqueous sodium hydroxide solution dropwise when stirring. And then add the mixed powder of 60% amount of mannitol, hydroxypropyl methyl cellulose and xanthan gum, disperse and then make it pass through 20 mesh sieve; finish granule after drying; add colloidal silica and mix uniformly. |

Example 22

Aripiprazole Suspension (2 Mg/Gram)

| | |
|---|---|
| Drug | Aripiprazole 2 g (0.2%[3], without pretreatment) |
| Excipient | Glycerin 54 g, Sucrose 15 g, Sodium Sulfite 0.5 g, Citric Acid Monohydrate 0.5 g, Tween 80 0.5 g, Polyethylene Glycol 6000 20 g, Sodium Benzoate 0.1 g, Sodium Carboxymethyl Cellulose 10 g |
| Medicament having acidic solution | 79% Aqueous ethanol solution 7.6 g |
| Solvent | Benzyl alcohol 5 g, Glycerin 6 g, Anhydrous ethanol 6 g, Water about 878 g |
| Acidifier | 10% Aqueous hydrochloric acid solution 1.8 g (molar ratio of it to aripiprazole is 1.1) |
| Alkalizer | 10% Aqueous Sodium hydroxide solution 2 g (molar ratio of it to hydrochloric acid is 1.0) |
| Preparation Technology | Mix sodium carboxymethyl cellulose, benzyl alcohol, sodium benzoate, 500 g water and 90% amount of glycerin to prepare the mixture of sodium carboxymethyl cellulose. Mix anhydrous ethanol, 10% amount of glycerin, Tween80, aqueous hydrochloric acid solution and aripiprazole to prepare medicament having acidic solution; add sodium hydrogen sulfite, citric acid monohydrate, polyethylene glycol and sucrose when stirring; add aqueous sodium hydroxide solution dropwise when stirring. Add the mixture of sodium carboxymethyl cellulose when stirring; finally add water until the total mass reaches 1000 g and uniformly mix. |

Examples 23

Prescription and Preparation Method of Aripiprazole Tablets (5 Mg/Tablet) (Unit: Gram)

| | |
|---|---|
| Drug | Aripiprazole 5 g (5.0%[1], without pretreatment) |
| Excipient | Lactose 20 g, Microcrystalline Cellulose 40 g, Hydroxypropyl-β-Cyclodextrins 30 g, Poloxamer188 0.2 g, Sodium Hydrogen Sulfite 0.05 g, Crosslinked carboxymethylcellulose Sodium 1 g, Talcum Powder 2.5 g, Magnesium Stearate 0.5 g |
| Medicament having acidic solution | 91% Aqueous ethanol solution 18.7 g |

-continued

| | |
|---|---|
| Solvent | 91% Aqueous ethanol solution 18.7 g (18.6%[2]) |
| Acidifier | 36% Hydrochloric acid 1.13 g (molar ratio of it to aripiprazole is 1.0) |
| Alkalizer | Sodium carbonate 1.06 g (molar ratio of it to hydrochloric acid is 0.90) |
| Preparation Technology | Mix 18 g 95% ethanol, poloxamer, hydrochloric acid and aripiprazole to prepare medicament having acidic solution; add sodium hydrogen sulfite, hydroxypropyl β-cyclo-dextrins and lactose when stirring to get mixture. Add the mixture into microcrystalline cellulose that is uniformly mixed with sodium carbonate and stir to get soft material, carry out extrusion granulation, finish granule after drying wet granules; add crosslinked carboxymethylcellulose sodium, talcum powder and magnesium stearate, mix uniformly and press. |

Example 24

Prescription and Preparation Method of Aripiprazole Tablets (5 Mg/Tablet) (Unit: Gram)

| | |
|---|---|
| Drug | Aripiprazole 5 g (4.0%[1], without pretreatment) |
| Excipient | Lactose 60 g, Microcrystalline Cellulose 35 g, starch 10 g, Povidone K30 0.1 g, Glycine 0.025 g, Hydroxypropyl cellulose 12 g, Sodium Thiosulfate 0.05 g, Magnesium Stearate 0.7 g |
| Medicament having acidic solution | 81% Aqueous ethanol solution 18.6 g |
| Solvent | 64% Aqueous ethanol solution 23.4 g (18.8%[2]) |
| Acidifier | 10% Aqueous hydrochloric acid solution 4.05 g (molar ratio of it to aripiprazole is 1.0) |
| Alkalizer | 20% Aqueous sodium carbonate solution 5.92 g (molar ratio of it to hydrochloric acid is 1.01) |
| Preparation Technology | Mix 15 g anhydrous ethanol, povidone, aqueous hydrochloric acid solution and aripiprazole to prepare medicament having acidic solution; add sodium thiosulfate, glycine and 40% amount of lactose when stirring; add aqueous sodium carbonate solution when stirring to get mixture. Add the mixture into the mixed powder of 60% amount of lactose, starch and microcrystalline cellulose and carry out stirring granulation; finish granule after drying wet granules; add hydroxypropyl cellulose and magnesium stearate, mix uniformly and press. |

Example 25

Prescription and Preparation Method of Aripiprazole Tablets (10 Mg/Tablet) (Unit: Gram)

| | |
|---|---|
| Drug | Aripiprazole 10 g (7.8%[1], without pretreatment) |
| Excipient | Lactose 65 g, Microcrystalline Cellulose 40 g, Carboxymethyl starch sodium 6 g, Sodium sulfite 0.15 g, Povidone K30 3 g, Magnesium Stearate 0.7 g, Colloidal silica 0.2 g |
| Medicament having acidic solution | 85% Aqueous ethanol solution 36.7 g |
| Solvent | 78% Aqueous ethanol solution 40.3 g (31.3%[2]) |
| Acidifier | 10% Aqueous hydrochloric acid solution 4.1 g (molar ratio of it to aripiprazole is 0.50), Citric Acid Monohydrate 2.42 g (molar ratio of it to aripiprazole is 0.52) |
| Alkalizer | 20% Aqueous sodium hydroxide solution 4.45 g (molar ratio of it to the acidifier is 0.98) |

-continued

| | |
|---|---|
| Preparation Technology | Mix 33 g 95% ethanol, aqueous hydrochloric acid solution, povidone, citric acid monohydrate and aripiprazole to prepare medicament having acidic solution; add sodium sulfite and 20% amount of lactose when stirring; add aqueous sodium hydroxide solution when stirring to get mixture. Add the mixture into the mixed powder of 80% amount of lactose, 50% amount of carboxymethyl starch sodium and microcrystalline cellulose and carry out stirring granulation; finish granule after drying wet granules; add magnesium stearate, colloidal silica and 50% amount of carboxymethyl starch sodium, mix uniformly and press. |

Example 26

Prescription and Preparation Method of Aripiprazole Tablets (5 Mg/Tablet) (Unit: Gram)

| | |
|---|---|
| Drug | Aripiprazole 5 g (4.3%[1], without pretreatment) |
| Excipient | Mannitol 60 g, Microcrystalline Cellulose 40 g, Carboxymethyl starch sodium 6 g, Sodium bisulfite 0.1 g, Sodium citrate dihydrate 0.05 g, Povidone K30 3 g, Magnesium Stearate 0.8 g |
| Medicament having acidic solution | 76% Aqueous ethanol solution 17.6 g |
| Solvent | 62% Aqueous ethanol solution 21.5 g (18.6%[2]) |
| Acidifier | 10% Aqueous hydrochloric acid solution 4.0 g (molar ratio of it to aripiprazole is 0.98) |
| Alkalizer | 10% Aqueous sodium hydroxide solution 4.29 g (molar ratio of it to hydrochloric acid is 9.8) |
| Preparation Technology | Mix 14 g 95% ethanol, aqueous hydrochloric acid solution, povidone K30 and aripiprazole to prepare medicament having acidic solution; stir when add sodium bisulfite, sodium citrate dihydrate and 20% amount of mannitol when stirring, then add aqueous sodium hydroxide solution when stirring to get mixture. Add the mixture into the mixed powder of 80% amount of mannitol, 50% amount of carboxymethyl starch sodium and microcrystalline cellulose and carry out stirring granulation; finish granule after drying wet granules; add magnesium stearate and 50% amount of carboxymethyl starch sodium, mix uniformly and press. |

Example 27

Prescription and Preparation Method of Aripiprazole Tablets (5 Mg/Tablet) (Unit: Gram)

| | |
|---|---|
| Drug | Aripiprazole 5 g (4.4%[1], without pretreatment) |
| Excipient | Lactose 60 g, Microcrystalline Cellulose 20 g, Starch 20 g, Sodium sulfite 0.05 g, Povidone K12 3 g, Hydroxypropyl cellulose 8 g, Magnesium Stearate 0.8 g, Colloidal silica 0.2 g |
| Medicament having acidic solution | 49% Aqueous ethanol solution 19.4 g |
| Solvent | 41% Aqueous ethanol solution 23.4 g (20.4%[2]) |
| Acidifier | 10% Aqueous hydrochloric acid solution 0.41 g (molar ratio of it to aripiprazole is 0.10) Citric Acid Monohydrate 2.16 g (molar ratio of it to aripiprazole is 0.92) |
| Alkalizer | 10% Aqueous sodium hydroxide solution 4.4 g (molar ratio of it to the acidifier is 0.99) |

-continued

| | |
|---|---|
| Preparation Technology | Mix 19 g 50% ethanol, aqueous hydrochloric acid solution, povidone K12, citric acid monohydrate and aripiprazole to prepare medicament having acidic solution; add sodium sulfite and 30% amount of lactose when stirring, then add aqueous sodium hydroxide solution when stirring to get mixture. Add the mixture into the mixed powder of 70% amount of lactose, starch, hydroxypropyl cellulose and microcrystalline cellulose and carry out stirring granulation; finish granule after drying wet granules; add magnesium stearate and colloidal silica, mix uniformly and press. |

Example 28

Prescription and Preparation Method of Aripiprazole Tablets (10 Mg/Tablet) (Unit: Gram)

| | |
|---|---|
| Drug | Aripiprazole 5 g (4.0%[1], without pretreatment) |
| Excipient | Lactose 70 g, Microcrystalline Cellulose 40 g, Carboxymethyl starch sodium 6 g, Sodium sulfite 0.2 g, Povidone K30 2 g, Magnesium Stearate 0.8 g, Colloidal silica 0.2 g |
| Medicament having acidic solution | 57% Aqueous ethanol solution 19.1 g |
| Solvent | 46% Aqueous ethanol solution 23.3 g (18.4%[2]) |
| Acidifier | 10% Aqueous hydrochloric acid solution 1.2 g (molar ratio of it to aripiprazole is 0.29) Citric Acid Monohydrate 1.7 g (molar ratio of it to aripiprazole is 0.72) |
| Alkalizer | 10% Aqueous sodium hydroxide solution 4.0 g (molar ratio of it to the acidifier is 0.88) 20% Aqueous sodium carbonate solution (molar ratio of it to the acidifier is 0.12) |
| Preparation Technology | Mix 18 g 60% ethanol, aqueous hydrochloric acid solution, citric acid monohydrate, povidone K30 and aripiprazole to prepare medicament having acidic solution; add sodium sulfite and 20% amount of lactose when stirring, then add aqueous sodium hydroxide solution and aqueous sodium carbonate solution when stirring to get mixture. Add the mixture into the mixed powder of 80% amount of lactose, 50% amount of carboxymethyl starch sodium and microcrystalline cellulose and carry out stirring granulation; finish granule after drying wet granules; add magnesium stearate, colloidal silica and 50% amount of carboxymethyl starch sodium, mix uniformly and press. |

Effect Example 1

Measure Particle Size of Aripiprazole in Aripiprazole Granules Compared by Comparison Examples 1 and 2, Examples 1 and 2

Test instruments: BT-9300S laser particle size distribution device (Dandong Bettersize Technology Ltd.); BT-800 automatic loop sampling system.

Test conditions: the medium of the loop sampling system is water, the volume is about 570 ml and the rotating speed of centrifugal pump is 1600 rpm.

Test method: Appropriate amount of sample is added into the loop sampling system and make the shading rate of the system come up to 15%±10. Treat with ultrasonic dispersion for 3 minutes, gain the average particle size with continuous sampling for 6 times.

| | particle size (μm) | | | |
|---|---|---|---|---|
| Sample | D[4, 3] | $D_{10}$ | $D_{50}$ | $D_{90}$ |
| Comparison example 1 | 87.08 | 14.22 | 76.52 | 179.30 |
| Comparison example 2 | 22.75 | 2.06 | 17.33 | 49.17 |
| Example 1 | 12.49 | 1.36 | 7.59 | 35.71 |
| Example 2 | 4.02 | 0.91 | 3.30 | 7.48 |

Note:
D[4, 3] is the volume mean diameter; $D_{10}$, $D_{50}$ and $D_{90}$ are the corresponding particle sizes when the percentage of cumulative particle size distribution is up to 10%, 50% and 90% respectively.

Effect Example 2

Comparison Experiments on Solubility (1) Measure the Solubility of Aripiprazole Preparations Prepared by Contrastive Examples 3 and 4, Examples 3~6, 9, 10 and 14

Method of measuring the solubility: take samples, according to solubility mensuration (Chinese Pharmacopoeia 2010 Volume 2 appendix X C Method 2), and 500 ml acetate buffer solution with the pH value of 4.0 (0.05 mol/L acetic acid–0.05 mol/L sodium acetate=16.4:3.6) as solvent. Rotation rate is 75 rpm. Carry on according to the mensuration. Take 5 ml solution at the 10th, 20th, 30th, 45th min respectively, and replenish 5 ml dissolution medium to dissolution cup. Filter the samples and take subsequent filtrate as sample solution. Prepare the reference solution. Detect respectively according to high-performance liquid chromatography (Chinese Pharmacopoeia 2010 Volume 2 appendix V D), and use octadecyl silane chemically bonded silica as filler. Use methanol—0.1% triethylamine solution (90:10) as mobile phase; detect at 255 nm, calculate the solubility of each tablet and record in the table below.

| | Solubility (%) | | | |
|---|---|---|---|---|
| Example | 10 min | 20 min | 30 min | 45 min |
| Contrastive example 3 | 33.7 | 45.3 | 56.0 | 73.4 |
| Contrastive example 4 | 56.1 | 85.5 | 95.1 | 97.8 |
| 3 | 60.8 | 87.7 | 97.2 | 99.1 |
| 4 | 71.4 | 92.5 | 98.6 | 99.8 |
| 5 | 70.4 | 92.9 | 98.6 | 99.7 |
| 6 | 60.2 | 87.8 | 94.9 | 98.8 |
| 8 | 61.8 | 90.4 | 95.8 | 98.7 |
| 9 | 59.2 | 88.4 | 95.4 | 98.1 |
| 10 | 67.9 | 91.5 | 97.8 | 99.5 |
| 14 | 73.7 | 98.9 | 99.7 | 99.8 |
| 28 | 61.1 | 89.5 | 98.0 | 99.3 |

The solubility of contrastive example 4 in which aripiprazole goes through microcrystalline processing in advance is better than that of contrastive example 3 in which aripiprazole is coarser, while the solubility of the examples in the present invention (Examples 3-6, 9-10 and 14) are all better than that of contrastive example 4. Wherein, improving the concentration of ethanol in the medicament having acidic solution and increase the dosage of povidone K30 is beneficial (example 5 in which the concentration of ethanol is improved is better than example 6, example 4 in which the concentration of ethanol is improved and the dosage of povidone is increased is better than example 3); improving the ratio of water-solution excipient is beneficial (example 10 is better than example 9); while the solubility of capsule is faster (example 14).

Effect Example 3

Comparison on Stability (1) Add samples into a high density polyethylene plastic bottle and pack. After the accelerated test for 3 months at 40'C±2° C. and under the relative humidity of 75%±5%, detect the state, content, solubility and related substance.

Determination method for content and the related substance: take appropriate dosage of samples and dissolve with ultrasonic shake in mobile phase, prepare the solution containing appropriate dosage of aripiprazole per ml as the test solution and the reference solution. Determination is respectively carried out by high-performance liquid chromatography (Chinese Pharmacopoeia 2010 Volume 2 appendix V D), and use octadecyl silane chemically bonded silica as filler; methanol-acetic acid solution (add 1 ml triethylamine to 1000 ml water, adjust pH to 4.0 with acetic acid) (60:40) as mobile phase. Detection wavelength is 255 nm, The determination of content is according to the external standard method, the determination of the related substance is calculated according to the main component self-calibrated method. The results are recorded in the table below.

| Example | State | | Content (%) | | Solubility at the $45^{th}$ min (%) | | Related Substance (%) | |
|---|---|---|---|---|---|---|---|---|
| | Prior to acceleration | After acceleration | Prior to acceleration | After acceleration | Prior to acceleration | After acceleration | Prior to acceleration | After acceleration |
| Contrastive 4 | White tablet | White tablet | 98.9 | 98.1 | 97.8 | 96.3 | 0.10 | 0.30 |
| 4 | White tablet | White tablet | 98.9 | 99.1 | 99.8 | 99.6 | 0.04 | 0.11 |
| 6 | White tablet | White tablet | 99.1 | 99.5 | 98.8 | 98.2 | 0.05 | 0.10 |
| 7 | White tablet | White tablet | 99.6 | 99.1 | 99.2 | 98.6 | 0.08 | 0.18 |
| 8 | White tablet | White tablet | 100.1 | 99.7 | 98.7 | 99.0 | 0.05 | 0.09 |
| 11 | White tablet | White tablet | 98.6 | 99.1 | 97.9 | 98.3 | 0.07 | 0.12 |
| 25 | White tablet | White tablet | 99.3 | 99.4 | 99.1 | 99.4 | 0.05 | 0.09 |
| 28 | White tablet | White tablet | 99.6 | 99.3 | 99.3 | 99.5 | 0.04 | 0.08 |

The amount of related substances (impurities) in the embodiments where antioxidants are used is significantly lower than that in contrastive example 4 where antioxidants are not used.

(2) Pack samples with high density polyethylene plastic bottle. After the accelerated test for 20 days at 60° C.±2° C., carry on the detection of state, content and related substance. Determination method is as above.

| Example | State | | Content (%) | | Related Substance (%) | |
|---|---|---|---|---|---|---|
| | Prior to acceleration | After acceleration | Prior to acceleration | After acceleration | Prior to acceleration | After acceleration |
| Contrastive 4 | White tablet | Off-white tablet | 98.9 | 98.4 | 0.10 | 0.26 |
| 4 | White tablet | Off-white tablet | 98.9 | 99.3 | 0.04 | 0.09 |
| 6 | White tablet | Off-white tablet | 99.1 | 99.3 | 0.05 | 0.11 |
| 7 | White tablet | Off-white tablet | 99.6 | 98.9 | 0.08 | 0.15 |
| 11 | White tablet | Off-white tablet | 98.6 | 99.1 | 0.07 | 0.12 |
| 14 | Content is white tablet | Content is off-white tablet | 99.5 | 99.6 | 0.04 | 0.09 |
| 21 | White fine particle | Off-white fine particle | 99.1 | 99.3 | 0.05 | 0.10 |
| 26 | White tablet | Off-white tablet | 99.5 | 99.4 | 0.04 | 0.08 |

The amount of related substances (impurities) in the embodiments where antioxidants are used is significantly lower than that in comparative example 4 where antioxidants are not used.

Effect Example 4 the Relationship Between Particle Size and Prescription & Operating Conditions The particle sizes of aripiprazole in samples are tested by the following method, and are relatively compared under the different prescriptions and operating conditions.

Test instruments: BT-9300S laser particle size distribution device (Dandong Bettersize Technology Ltd.); BT-800 automatic loop sampling system.

Test condition: the medium of the loop sampling system is water, the volume is about 570 ml and the rotating speed of centrifugal pump is 1600 rpm.

Test method: Appropriate amount of sample is added into the loop sampling system and make the shading rate of the system come up to 15%±10. Treat with ultrasonic dispersion for 3 minutes. Gain the average particle size with continuous sampling for 6 times.

D[4,3] is the volume mean diameter; $D_{10}$, $D_{50}$ and $D_{90}$ are the corresponding particle sizes when the percentage of cumulative particle size distribution is up to 10%, 50% and 90% respectively.

The comparison experiments and results are as follows: (the concentration of aqueous ethanol solution is the concentration of the solvent contained in the medicament having acidic solution; and other excipients contained in medicament having acidic solution are surfactant and/or solubilizer).

1. 10 g Aripiprazole, 5 g Povidone K30, hydrochloric acid, water and ethanol are used to prepare medicament having acidic solution (the molar ratio of hydrochloric acid to aripiprazole is 1:1. The dosage of aqueous ethanol solution is 38.9 g, which is 3.89 times the mass of aripiprazole). 10% Aqueous sodium hydroxide solution (the molar ratio of sodium hydroxide to hydrochloric acid is 1.01) is added when stirring (the linear speed of stirrer is 160 m/min) to prepare the mixture solution and test the particle size of the sample. When the concentration of aqueous ethanol solution is 50%, a 50° C. water-bath is used. The results of comparison experiments refer to table 1.

TABLE 1 the comparison of particle sizes

| Number | Concentration of aqueous ethanol solution (W/W %) | Particle size (μm) | | | |
|---|---|---|---|---|---|
| | | D[4, 3] | $D_{10}$ | $D_{50}$ | $D_{90}$ |
| 1-1 | 50 | 25.32 | 3.98 | 20.43 | 44.72 |
| 1-2 | 75 | 30.19 | 4.07 | 26.70 | 63.13 |
| 1-3 | 85 | 32.46 | 4.73 | 28.59 | 68.61 |
| 1-4 | 90 | 28.69 | 4.23 | 24.09 | 59.83 |
| 1-5 | 95 | 18.93 | 2.37 | 16.3 | 39.06 |

Table 1 shows that the particle size is affected by the concentration of aqueous ethanol solution, and the particle size is the smallest when the concentration reaches 95%.

2. 10 g Aripiprazole, 30 g anhydrous ethanol, 2 g povidone K30, 8.9 g 10% hydrochloric acid (the molar ratio of hydrochloric acid to aripiprazole is 1.1) are used to prepare medicament having acidic solution. 30 g Lactose is added when stirring, and then 10% aqueous sodium hydroxide solution (the molar ratio of sodium hydroxide to hydrochloric acid is 1.01) is added when stirring to prepare the mixture solution. Test the particle sizes of the prepared samples. The results of comparison experiments refer to table 2.

TABLE 2 the comparison of particle sizes

| Number | Concentration of aqueous ethanol solution (W/W %) | Line speed of stirrer (m/min) | Particle size (μm) | | | |
|---|---|---|---|---|---|---|
| | | | D[4,3] | $D_{10}$ | $D_{50}$ | $D_{90}$ |
| 2-1 | 79 | 50 | 37.86 | 6.27 | 28.83 | 83.25 |
| 2-2 | 79 | 160 | 33.68 | 4.16 | 27.64 | 72.86 |
| 2-3 | 79 | 285 | 29.85 | 3.41 | 23.25 | 66.11 |

Table 2 shows that the relationship of the particle size and the stirring speed is as follows: with the increase of the stirring speed, the particle size will have a tendency of increase.

3. 10 g Aripiprazole, 30 g anhydrous ethanol, 8.9 g 10% hydrochloric acid (the molar ratio of hydrochloric acid to aripiprazole is 1.1, and the concentration of aqueous ethanol solution is 79%, the dosage of which is 3.89 times the mass of aripiprazole) are used to prepare medicament having acidic solution. Excipient (2) and excipient (1) are added when stirring, and 10% aqueous sodium hydroxide solution (the molar ratio of sodium hydroxide to hydrochloric acid is 1.01) is added when stirring (the line speed of stirrer is 160 m/min) to prepare the mixture solution. Test the particle sizes of the prepared samples. The results of comparison experiments refer to table 3, wherein excipient (1) refers to the main water-soluble carrier, excipient (2) refers to the excipients, surfactant, solubilizer and PEG 6000 contained in the medicament having acidic solution.

Medicament: (1) refers to the mass ratio of aripiprazole to excipient (1); Medicament: (2) refers to the mass ratio of aripiprazole to excipient (2).

TABLE 3 the comparison of particle sizes

| Number | Excipient (1) | Excipient (2) | Medicament: (1) | Medicament: (2) | Particle size (μm) | | | |
|---|---|---|---|---|---|---|---|---|
| | | | | | D[4,3] | $D_{10}$ | $D_{50}$ | $D_{90}$ |
| 3-1 | lactose | — | 1:0.5 | — | 45.21 | 5.17 | 32.51 | 104.83 |
| 3-2 | lactose | — | 1:1 | — | 40.01 | 5.79 | 30.41 | 88.26 |
| 3-3 | lactose | — | 1:2 | — | 35.21 | 5.13 | 27.2 | 77.36 |
| 3-4 | lactose | — | 1:3 | — | 33.78 | 4.81 | 27.18 | 72.6 |

TABLE 3-continued the comparison of particle sizes

| Excipient Number | Excipient (1) | Excipient (2) | Medicament: (1) | Medicament: (2) | Particle size (μm) | | | |
|---|---|---|---|---|---|---|---|---|
| | | | | | D[4,3] | $D_{10}$ | $D_{50}$ | $D_{90}$ |
| 3-5 | lactose | — | 1:6 | — | 23.72 | 2.73 | 18.91 | 51.6 |
| 3-6 | lactose | — | 1:9 | — | 11.49 | 2.01 | 9.54 | 22.76 |
| 3-7 | lactose | povidone K30 | 1:3 | 1:0.2 | 33.68 | 4.16 | 27.64 | 72.86 |
| 3-8 | lactose | povidone K30 | 1:3 | 1:1 | 28.23 | 3.76 | 20.42 | 64.12 |
| 3-9 | lactose | povidone K30 | 1:3 | 1:2 | 14.85 | 1.61 | 11.28 | 32.9 |
| 3-10 | lactose | povidone K30 | 1:3 | 1:0.5 | 28.44 | 3.93 | 22.47 | 61.34 |
| 3-11 | lactose | povidone K30 | 1:6 | 1:0.5 | 15.29 | 1.46 | 11.52 | 48.64 |
| 3-12 | lactose | povidone K30 | 1:9 | 1:0.5 | 6.73 | 1.15 | 5.06 | 15.52 |
| 3-13 | lactose | Sodium dodecyl sulfate | 1:6 | 1:0.2 | 33.08 | 4.73 | 27.8 | 67.26 |
| 3-14 | lactose | Tween-80 | 1:6 | 1:0.2 | 21.14 | 2.69 | 12.97 | 51.97 |
| 3-15 | lactose | PEG 6000 | 1:6 | 1:1 | 17.03 | 2.52 | 14.02 | 36.15 |
| 3-16 | lactose | PEG 6000 | 1:6 | 1:4 | 7.1 | 1.66 | 5.86 | 14.74 |
| 3-17 | lactose | Poloxamer 188 | 1:6 | 1:0.2 | 25.12 | 2.38 | 16.36 | 60.45 |
| 3-18 | lactose | Hydroxypropyl β-Cyclodextrin | 1:6 | 1:1 | 26.73 | 2.91 | 16.96 | 64.78 |
| 3-19 | lactose | Hydroxypropyl β-Cyclodextrin | 1:6 | 1:4 | 18.65 | 1.78 | 15.33 | 41.4 |

Table 3 shows that when one of the surfactant, solubilizer and water-soluble carrier of solid dispersions is added in the medicament having acidic solution, the particle size will be reduced with the increase of the dosage of the said excipient. (2) When at least two of the surfactant, solubilizer and water-soluble carrier of solid dispersions are added in the medicament having acidic solution, under the case that the dosage of one excipient is unchangeable, the particle size will be reduced with the increase of the dosage of the other excipients; (3) When medicament: lactose is 1:6 and medicament: Tween-80 (or poloxamer or sodium dodecyl sulfate) is 1:0.2, the particle size will be decreased more when Tween-80 is added than poloxamer is, and poloxamer is than sodium dodecyl sulfate is.

4. 10 g Aripiprazole, 30 g anhydrous ethanol, 8.9 g 10% hydrochloric acid (the molar ratio of hydrochloric acid to aripiprazole is 1.1, and the concentration of aqueous ethanol solution is 79%, the dosage of which is 3.89 times the mass of aripiprazole) and 5 g povidone K30 are used to prepare medicament having acidic solution. Excipient (1) is added when stirring, and 10% aqueous sodium hydroxide solution (the molar ratio of sodium hydroxide to hydrochloric acid is 1.01) is added when stirring (the line speed of stirrer is 160 m/min) to prepare the mixture solution. Test the particle sizes of the prepared samples. The results of comparison experiments refer to table 4.

TABLE 4 the comparison of particle sizes

| Excipient Number | Medicament: (1) | Particle size (μm) | | | |
|---|---|---|---|---|---|
| | | D[4,3] | $D_{10}$ | $D_{50}$ | $D_{90}$ |
| 4-1 | lactose | 1:3 | 28.44 | 3.93 | 22.47 | 61.34 |
| 4-2 | lactose | 1:6 | 15.29 | 1.46 | 11.52. | 48.64. |
| 4-3 | lactose | 1:9 | 6.73 | 1.15 | 5.06 | 15.52 |
| 4-4 | mannitol | 1:2 | 30.68 | 3.4 | 22.19 | 70.32 |
| 4-5 | mannitol | 1:4 | 25.26 | 2.24 | 12.25 | 66.43 |
| 4-6 | mannitol | 1:6 | 11.73 | 1.14 | 5.07 | 37.82 |
| 4-7 | maltitol | 1:3 | 36.85 | 4.77 | 27.42 | 83.74 |
| 4-8 | maltitol | 1:6 | 25.74 | 3.02 | 15.95 | 64.12 |
| 4-9 | maltitol | 1:9 | 26.3 | 2.16 | 13.06 | 68.9 |
| 4-10 | sucrose | 1:3 | 32.33 | 3.98 | 25.31 | 71.7 |
| 4-11 | sucrose | 1:6 | 31.74 | 2.78 | 23.44 | 73.58 |
| 4-12 | sucrose | 1:9 | 9.95 | 0.98 | 6.61 | 22.56 |

Note: columns are Excipient Number | Medicament: (1) ratio | D[4,3] | D10 | D50 | D90.

Table 4 shows that (1) when one of mannitol, lactose, maltitol and sucrose is added in the medicament having acidic solution, the particle size will be reduced with the increase of the dosage of the said excipient; (2) When small particle size of aripiprazole is required, mannitol is better than lactose, lactose is better than maltitol, and maltitol is better than sucrose.

5. Take part of the mixture solution prepared by the example above, add 4 times the amount of excipient (1) that is previously added to each prescription and carry out stirring granulation. Finish granule after drying wet granules. Test the particle size of the sample. The results of comparison experiments refer to table 5.

TABLE 5 the comparison of particle sizes

| Number | Excipient (1) | Excipient (2) | Particle size (μm) | | | |
|---|---|---|---|---|---|---|
| | | | D[4,3] | $D_{10}$ | $D_{50}$ | $D_{90}$ |
| 3-6 | lactose | — | 10.12 | 1.93 | 8.17 | 19.34 |
| 3-9 | lactose | Povidone K30 | 13.29 | 1.26 | 10.5 | 25.34. |
| 3-14 | lactose | Tween-80 | 17.73 | 2.14 | 10.06 | 38.62 |
| 3-16 | lactose | PEG 6000 | 6.23 | 1.19 | 4.15 | 12.33 |
| 4-6 | mannitol | Povidone K30 | 9.38 | 1.02 | 4.31 | 27.89 |
| 4-8 | maltitol | Povidone K30 | 22.85 | 2.76 | 12.49 | 50.75 |
| 4-11 | sucrose | Povidone K30 | 28.56 | 2.14 | 20.48 | 58.21 |

6. Repeat Tests and Results 10 g Aripiprazole, 30 g anhydrous ethanol, 8.5 g 10% aqueous hydrochloric acid (the molar ratio of hydrochloric acid to aripiprazole is 1.05) and 5 g povidone K30 are used to prepare medicament having acidic solution. 60 g Lactose is added when stirring (the line speed of stirrer is 160 m/min), and 9.3 g 10% aqueous sodium hydroxide solution (the molar ratio of sodium hydroxide to hydrochloric acid is 1.0) is added quickly, keep stirring for 2 mins to prepare the mixture solution, and then 340 g lactose is added, stir until soft material is prepared, and carry out extrusion granulation, finish granule after drying wet granules, test the particle size of the sample. The experiment is repeated for five times and compare the results in table 6.

TABLE 6 the comparison of particle sizes

| Number | Particle size (μm) | | | |
|---|---|---|---|---|
| | D[4, 3] | $D_{10}$ | $D_{50}$ | $D_{90}$ |
| 6-1 | 16.55 | 1.46 | 7.17 | 49.05 |
| 6-2 | 12.26 | 1.47 | 7.06 | 31.51 |
| 6-3 | 14.01 | 1.38 | 6.85 | 40.79 |
| 6-4 | 13.35 | 1.38 | 6.75 | 37.69 |
| 6-5 | 11.28 | 1.21 | 6.07 | 29.54 |
| Average value | 13.49 | 1.38 | 6.78 | 37.72 |
| RSD (%) | 13.28 | 6.75 | 5.68 | 18.49 |

The invention claimed is:

1. A method for preparing an aripiprazole medicament formulation, which comprises the following steps: dissolving aripiprazole in an acidic solution having an acidifier so as to obtain a medicament having acidic solution; then, performing a wet granulation on or preparing a suspension with the obtained medicament having acidic solution, an alkalizer, and an excipient so as to obtain the aripiprazole medicament formulation; said excipient comprising an antioxidant.

2. The method according to claim 1, wherein said antioxidant is selected from the group consisting of sodium metabisulfite, sodium bisulfite, sodium sulfite, thiourea, sodium thiosulfate, L-cysteine and sodium ascorbate, water-soluble organic weak acid, the conjugate base of the water-soluble organic weak acid, butylated hydroxyanisole, dibutyl hydroxy toluene, ascorbyl palmitate and propyl gallate; said water-soluble organic weak acid is selected from the group consisting of citric acid, tartaric acid and malic acid; said conjugate base of the water-soluble organic weak acid is sodium citrate and/or sodium tartrate.

3. The method according to claim 1, wherein said antioxidant is added after the preparation of said medicament having acidic solution, and before or during the time when said alkalizer is added; the amount of said antioxidant is 0.1 to 100% of the mass of aripiprazole; when performing wet granulation, the amount of said antioxidant is 0.1 to 10% of the mass of aripiprazole; when preparing said suspension, the amount of said antioxidant is 10 to 100% of the mass of aripiprazole.

4. The method according to claim 1, wherein said acidifier is selected from the group consisting of hydrochloric acid, citric acid, malic acid, lactic acid, hydrobromic acid, nitric acid, sulfuric acid, fumaric acid, succinic acid, maleic acid, acetic acid and phosphoric acid; the amount of said acidifier is 1 to 1.2 times the minimum amount which can completely dissolve the aripiprazole.

5. The method according to claim 4, wherein the acidifier is hydrochloric acid, the molar ratio of the hydrochloric acid to aripiprazole is 0.9 to 1.2; when the acidifier is hydrochloric acid and citric acid, a molar ratio of the hydrochloric acid and citric acid to aripiprazole is 0.9 to 1.2.

6. The method according to claim 1, wherein the solvent of said acidic solution having an acidifier is organic solvent, or a mixture of water and organic solvent; said organic solvent is an acceptable solvent in the pharmaceutical field in which the solubility of aripiprazole in said solvent is greater than the solubility of aripiprazole in water; the solvent dosage of the acidic solution having an acidifier is 2 times or more the mass of aripiprazole.

7. The method according to claim 6, wherein the solvent of said acidic solution having an acidifier is aqueous ethanol solution with an ethanol concentration of 40 wt % or more.

8. The method according to claim 1, wherein before the alkalizer is added, adding one or more selected from the group consisting of surfactant, solubilizer, a water-soluble carrier and disintegrant; said surfactant and/or solubilizer is selected from the group consisting of povidone, sodium dodecyl sulfate, poloxamer, polyoxyethylenated castor oil, Tween 80 and polyoxyl (40) stearate; said water-soluble carrier is selected from the group consisting of lactose, mannitol, sucrose, polyethylene glycol, hydroxypropyl-β-cyclodextrin, β-cyclodextrin and maltitol; said disintegrant is selected from the group consisting of sodium carboxymethyl starch, hydroxypropyl cellulose, cross-linked polyvinylpyrrolidone and cross-linked carboxymethyl cellulose sodium.

9. The method according to claim 8, wherein said surfactant, said solubilizer, polyethylene glycol and hydroxypropyl-β-cyclodextrin are added during or after the preparation of the medicament having acidic solution; said water-soluble carrier and/or disintegrant are added after the preparation of the medicament having acidic solution except for polyethylene glycol and hydroxypropyl-β-cyclodextrin.

10. The method according to claim 8, wherein the amount of said surfactant and/or solubilizer is 0.01 to 2 times the mass of aripiprazole; the amount of said water-soluble carrier is 1 to 10 times the mass of aripiprazole.

11. The method according to claim 1, wherein while preparing the medicament having acidic solution, increasing the temperature to 30 to 85° C.

12. The method according to claim 1, wherein said alkalizer refers to inorganic strong alkali and/or the salt of weak acid and strong alkali, said inorganic strong alkali is sodium hydroxide and/or potassium hydroxide, said salt of strong alkali and weak acid is selected from the group consisting of sodium carbonate, potassium carbonate and disodium hydrogen phosphate; said alkalizer is sodium hydroxide and/or sodium carbonate.

13. The method according to claim 1, wherein said alkalizer is added in the form of alkalizer-containing solution with a concentration between 5 to 20 wt %; the solvent contained in the alkalizer-containing solution is water or a mixture of water and organic solvent; wherein
said organic solvent is the acceptable solvent in the pharmaceutical field in which the solubility of aripiprazole is larger than in water.

14. The method according to claim 13, wherein the subsequent steps require wet granulation, the total amount of the solvent contained in the medicament having acidic solution and said alkalizer-containing solution is 5 to 100% of the mass of dry materials of wet granulation.

15. The method according to claim 1, wherein a pairing of said acidifier and said alkalizer is selected from the group consisting of:
Type 1: the acidifier is inorganic strong acid, said alkalizer is inorganic strong alkali;
Type 2: said acidifier is inorganic strong acid, said alkalizer is the salt of weak acid and strong alkali;
Type 3: said acidifier is organic weak acid, said alkalizer is inorganic strong alkali; and
Type 4: said acidifier is inorganic strong acid and organic weak acid, said alkalizer is one or two of inorganic strong alkali and the salt of weak acid and strong alkali.

16. The method according to claim 15, wherein in type 1, after the preparation of the medicament having acidic solution, before or during the time when the alkalizer is added, adding a reagent selected from the group consisting of organic weak acid, acid salt and a conjugate base of organic weak acid, said organic weak acid is selected from the group consisting of citric acid, glycine, tartaric acid, malic acid and acetic acid; said acid salt is selected from the group consisting of sodium bisulfite, sodium sulfite, sodium dihydrogen phosphate and disodium hydrogen phosphate, said conjugate base of organic weak acid is sodium citrate, an amount of the reagent is between 0.1% to 0.4% of the mass of aripiprazole.

17. The method according to claim 1, wherein while performing wet granulation, the amount of aripiprazole is 1% to 20% of the mass of the dry materials of wet granulation; while preparing said suspension, the amount of aripiprazole is 0.01% to 1% of the mass of the suspension.

18. The method according to claim 1, wherein the specific operation of wet granulation is selected from the group consisting of:
   method (1) uniformly mixing the medicament having acidic solution with the alkalizer or an alkalizer-containing solution to obtain a granulating solution, and then carrying on extrusion granulation, stirring granulation, fluidized spray granulation or centrifugal spray granulation with the granulating solution and the excipient to obtain the aripiprazole medicament formulation;
   method (2) uniformly mixing the medicament having acidic solution with the excipient, and then uniformly mixing them with the alkalizer or an alkalizer-containing solution, and carrying on extrusion granulation or stirring granulation to obtain the aripiprazole medicament formulation;
   method (3) uniformly mixing the alkalizer or an alkalizer-containing solution with the excipient, and then uniformly mixing them with the medicament having acidic solution, and carrying on extrusion granulation or stirring granulation to obtain the aripiprazole medicament formulation; and
   method (4) uniformly mixing the medicament having acidic solution, one-third or less than one-third of the excipient, with the alkalizer or an alkalizer-containing solution, and then mixing the resulted mixture with the rest of the excipient and carrying on extrusion granulation or stirring granulation to obtain the aripiprazole medicament formulation;
   said aripiprazole medicament formulation is solid particles preparations, tablets, dry suspensions or capsules.

19. The method according to claim 18, wherein when said aripiprazole medicament formulation is solid particle preparation, said excipient is filler; when said aripiprazole medicament formulation is tablet or capsule, said excipient is filler, disintegrant and lubricant; when said aripiprazole medicament formulation is dry suspension, said excipient is suspending agent and lubricant.

20. The method according to claim 19, wherein in said solid preparation, the amount sum of said filler and a water-soluble carrier is 70 to 90% of the mass of aripiprazole solid preparation; the total amount of said disintegrant is 1 to 10% of the mass of aripiprazole solid preparation; the amount of said lubricant is 0.2 to 3% of the mass of aripiprazole solid preparation; the amount of said suspending agent is 85 to 95% of the mass of the dry suspension.

21. The method according to claim 18, wherein the solid particles preparations, dry suspensions, tablets or capsules are prepared by wet granulation, the method comprises the following steps: (1) dissolving aripiprazole in aqueous ethanol solution having hydrochloric acid to obtain the medicament having acidic solution; (2) adding a water-soluble carrier, antioxidant and alkalizer to get a mixture, the water-soluble carrier and antioxidant being added before or during the time when the alkalizer is added; (3) carrying on wet granulation with said mixture and said excipient to obtain the solid particles preparations, or carrying on wet granulation and pressing to obtain tablets, or carrying on wet granulation and loading capsules to obtain capsules; or carrying on wet granulation with the mixture and the excipient to obtain dry suspensions of aripiprazole; wherein the alkalizer is sodium hydroxide and/or sodium carbonate; when said alkalizer is sodium hydroxide, said alkalizer is added in the form of aqueous sodium hydroxide solution, a molar ratio of hydrochloric acid to aripiprazole is between 0.95 to 1.1, a molar ratio of said alkalizer to hydrochloric acid is 0.99 to 1.02.

22. The method according to claim 21, wherein in step (1), said medicament having acidic solution also contains a surfactant and/or a solubilizer; said medicament having acidic solution also contains a water-soluble carrier: polyethylene glycol 6000 and/or hydroxypropyl-β-cyclodextrin; in step (2), said mixture also contains a disintegrant, said disintegrant is added before or during the time when the alkalizer is added.

23. The method according to claim 21, wherein in step (3), when the solid particle preparations, tablets or capsules are prepared, a filler is selected from the group consisting of lactose, microcrystalline cellulose, starch and mannitol, the total amount of said filler and said water-soluble carrier in step (1) and step (2) is 80 to 90% of the mass of the solid particles preparation, tablet or capsule of aripiprazole; a disintegrant is selected from the group consisting of sodium carboxymethyl starch, hydroxypropyl cellulose, cross-linked polyvinylpyrrolidone and crosslinked carboxymethylcellulose sodium, whose amount is 1 to 10% of the mass of tablet or capsule of aripiprazole; a lubricant is selected from the group consisting of colloidal silica, sodium stearyl fumarate, talcum powder and magnesium stearate, whose amount is 0.5 to 3% of the mass of tablet or capsule of aripiprazole; when dry suspension is prepared, a suspending agent is selected from the group consisting of xanthan gum, mannitol and hydroxypropyl methyl cellulose; said lubricant is colloidal silica; the amount of said suspending agent is 90 to 96% of the mass of the dry suspension; the amount of said lubricant is 0.2 to 0.5% of the mass of the dry suspension.

24. The method according to claim 1, wherein a suspension is prepared, said excipients includes 5 to 25% suspending agent, 0 to 0.5% wetting agent, 0 to 0.3% preservative, 0 to 3% corrective agent and solvent, an amount of the solvent is to complement a weight percent of the suspension up to 100%, the percentage is a mass percentage relative to the suspension.

25. The method according to claim 24, wherein said suspending agent is selected from the group consisting of xanthan gum, arabic gum, povidone, tragacanth, sodium alginate, glycerin, sucrose, mannitol, sorbitol, methyl cellulose, hydroxypropyl methyl cellulose, carboxymethyl starch sodium, carboxymethyl cellulose sodium and silicon bentonite; said wetting agent is selected from the group consisting of Tween 80, polyoxyethylene aliphatic alcohol ether, polyoxyethylene fatty acid, poloxamer and sodium dodecyl sulfate; said solvent is water or the mixture of water and alcohol; the preservative is selected from the group consisting of benzoic acid, sodium benzoate, propyl hydroxybenzoate, sodium propyl hydroxybenzoate, methyl hydroxybenzoate and sodium methyl hydroxybenzoate and sorbic acid; said corrective agent is selected from the group consisting of aspartame, stevia and flavors.

26. The method according to claim 24, wherein the specific operation of preparing the suspension refers to any one of the following methods: method (1) uniformly mixing the medicament having acidic solution with the alkalizer or an alkalizer-containing solution, and then mixing them with the suspending agent; method (2) uniformly mixing the medicament having acidic solution with a water-soluble carrier and/or disintegrant, and then uniformly mixing them with the alkalizer or an alkalizer-containing solution, further mixing them with the suspending agent; method (3) mixing the medicament having acidic solution with the water-soluble carrier and/or disintegrant, and also with the suspending agent, and then mixing them with the alkalizer or an alkalizer-containing solution; wherein said suspending agent is obtained by mixing other excipients contained in said suspending agent with the suspending agent; in this process of preparing said suspension, dispersing treatment is carried out with a colloid mill or a homogenizer.

27. The method according to claim 24, comprising the following steps: (1) dissolving aripiprazole in the solution having an acidifier so as to obtain a medicament having acidic solution; (2) adding a water-soluble carrier, said antioxidant and said alkalizer to obtain a mixture, the water-soluble carrier and the antioxidant being added before or during the time when the alkalizer is added; (3) mixing the mixture with said suspending agent; wherein, said alkalizer is sodium hydroxide, said sodium hydroxide is added in the form of aqueous sodium hydroxide solution with a concentration of 5 to 20 wt %; said acidifier is hydrochloric acid and/or lactic acid; the molar ratio of the alkalizer to hydrochloric acid is 0.99 to 1.02, in step (1), the solvent in the medicament having acidic solution is selected from the following alcohols, or selected from the aqueous solution of the following alcohols: ethanol, propylene glycol, glycerol and benzyl alcohol.

28. The method according to claim 27, wherein in step (1), said medicament having acidic solution also contains a surfactant and/or a solubilizer; the concentration of alcohol in said aqueous alcohol solution is 70 wt % or more; said medicament having acidic solution also contains a water-soluble carrier: polyethylene glycol 6000; in step (2), said water-soluble carrier is selected from the group consisting of sucrose, mannitol and polyethylene glycol 6000; said antioxidant is selected from the group consisting of sodium bisulfite, sodium sulfite, sodium ascorbate, L-cysteine and sodium thiosulfate; the amount of said antioxidant is 10 to 100% of the mass of aripiprazole; in step (3), said suspending agent is selected from the group consisting of xanthan gum, hydroxypropyl methyl cellulose, sucrose and sodium carboxymethyl cellulose, the amount of said suspending agent is 1 to 15.5% of the mass of the suspension.

29. The aripiprazole medicament formulation prepared by the method according to claim 1.

30. The method according to claim 2, wherein said antioxidant is one selected from the group consisting of sodium bisulfite, sodium metabisulfite, sodium sulfite and sodium thiosulfate in combination with said water-soluble organic weak acid, or in combination with said water-soluble organic weak acid and said conjugated base of this water-soluble organic weak acid.

31. The method according to claim 15, wherein the pairing of said acidifier and said alkalizer is selected from the group consisting of:
Type 1: hydrochloric acid and sodium hydroxide, a molar ratio of sodium hydroxide to hydrochloric acid is 0.95 to 1.05;
Type 2: hydrochloric acid and sodium carbonate, or hydrochloric acid and disodium hydrogen phosphate, a molar ratio of sodium carbonate or disodium hydrogen phosphate to hydrochloric acid is 0.75 to 1.05;
Type 3: lactic acid and sodium hydroxide, a molar ratio of the sodium hydroxide to the lactic acid is 0.95 to 1.05; and
Type 4: said acidifier is hydrochloric acid and citric acid, said alkalizer is sodium hydroxide, or the combination of sodium hydroxide and sodium carbonate, a molar ratio of said alkalizer to said acidifier is 0.95 to 1.05.

* * * * *